(12) United States Patent
Docherty

(10) Patent No.: US 10,285,586 B2
(45) Date of Patent: May 14, 2019

(54) REGISTRATION ACROSS FRAME BOUNDARIES IN AO-SLO CAPTURE

(71) Applicant: CANON KABUSHIKI KAISHA, Tokyo (JP)

(72) Inventor: Andrew Docherty, St Leonards (AU)

(73) Assignee: Canon Kabushiki Kaisha, Tokyo (JP)

( * ) Notice: Subject to any disclaimer, the term of this patent is extended or adjusted under 35 U.S.C. 154(b) by 330 days.

(21) Appl. No.: 14/979,220

(22) Filed: Dec. 22, 2015

(65) Prior Publication Data

US 2016/0183780 A1   Jun. 30, 2016

(30) Foreign Application Priority Data

Dec. 24, 2014   (AU) ................................ 2014280958

(51) Int. Cl.
   *A61B 3/14*   (2006.01)
   *A61B 3/12*   (2006.01)
   *G02B 27/00*   (2006.01)

(52) U.S. Cl.
   CPC ............ *A61B 3/12* (2013.01); *G02B 27/0093* (2013.01)

(58) Field of Classification Search
   CPC ..... G06T 7/0012; G06T 7/0016; G06T 7/246; G06T 7/337; G06T 3/0018; G06T 5/003; G06T 2207/20201; H04N 5/2329; H04N 5/2628; H04N 5/23238; H04N 5/23248; H04N 5/23254; H04N 5/23258; H04N 5/23267; A61F 9/008; G02B 27/0093; G01B 9/02055; G06K 9/0061; A61B 3/0025; A61B 3/12; A61B 3/14; A61B 3/102; A61B 3/113; A61B 3/145

USPC .......... 351/206–209, 246; 348/208.2, 208.4, 348/241, 497; 356/497; 382/275

See application file for complete search history.

(56) References Cited

U.S. PATENT DOCUMENTS

| 8,358,359 | B2 | 1/2013 | Baker et al. |
| 2005/0270486 | A1* | 12/2005 | Teiwes ................. A61B 3/113 351/209 |
| 2011/0211082 | A1 | 9/2011 | Forssen et al. |

(Continued)

OTHER PUBLICATIONS

Debasish Dasgupta, Australian FSR Patent Examination Report, dated Aug. 26, 2016; IP Australia, pp. 1-4.

(Continued)

*Primary Examiner* — Mustak Choudhury
(74) *Attorney, Agent, or Firm* — Canon U.S.A., Inc. IP Division

(57) ABSTRACT

A method of compensating for distortion, in a plurality of retinal image frames, arising from eye movement receives at least one reference image frame and plural other image frames of the eye. For each frame, the method determines a plurality of shifts relative to the reference image frame, and an initial eye movement trajectory based on at least an initial reference frame distortion, and the shifts within each of said other image frames. The method estimates a current reference frame distortion using the initial trajectory and the shifts within each of the other image frames, and a current eye movement trajectory based on the estimated current reference frame distortion, and the shifts within each of said other image frames to provide a smooth transition between the other image frames in the eye movement. With this the method compensates for distortion in said frames using the current eye movement trajectory.

19 Claims, 17 Drawing Sheets

(56) References Cited

U.S. PATENT DOCUMENTS

2013/0071004 A1* 3/2013 Yonezawa ............ G06K 9/0061
                                                    382/133
2013/0128222 A1* 5/2013 Huang ................. A61B 3/1005
                                                    351/206
2014/0063460 A1    3/2014 Borycki et al.

OTHER PUBLICATIONS

Sun; Liu, Rolling Shutter Distortion Removal Based on Curve Interpolation, IEEE Trans. Consumer Electron.; vol. 58, No. 3, pp. 1045.

* cited by examiner

REGISTRATION ACROSS FRAME BOUNDARIES IN AO-SLO CAPTURE

REFERENCE TO RELATED PATENT APPLICATION(S)

This application claims the benefit under 35 U.S.C. § 119 of the filing date of Australian Patent Application No. 2014280958, filed Dec. 24, 2014, hereby incorporated by reference in its entirety as if fully set forth herein.

TECHNICAL FIELD

This invention concerns the image stabilization of videos of a retina for image analysis and, in particular, the compensation of scene motion in a video sequence for further alignment and processing.

BACKGROUND

Scanning-laser ophthalmoscopes (SLO) are medical devices which are becoming increasingly common and increasingly useful for the visualization of the retina. A recent innovation is to combine the SLO with adaptive optics (AO) which compensates for the optical distortions of the eye to provide an unprecedented view of the retina in-vivo. Such an AO-SLO device is able to take images of a retina with a resolution in the order of microns, enabling the doctor to observe images of the retina that can resolve individual photoreceptors.

The AO-SLO can capture images of the retina continuously and therefore is often used to take video sequences of the retina, where a video sequence may be a sequence of consecutively captured still images. This enables the doctor to view the change of the retina at a microscopic scale and see, for example, the transit of blood cells through the retinal blood vessels, and conduct subsequent measurement of the velocity of blood flow.

To form the image of the retina, an AO-SLO device scans a laser in a raster pattern over a small area on the surface of the retina and detects the amount of light returned. A representative device has an oscillating mirror driven at a frame rate of approximately 60 Hz, with a resonant scanner forming scan-lines at a rate of 12 kHz and a pixel clock of 5 MHz. This device captures a video at 60 frames per second comprising images of a representative size of 400×400 pixels.

While the AO-SLO is able to compensate for aberrations of the vision-forming lens and cornea of the eye, it cannot compensate for image distortion caused by the movement of the eye. The human eye is in constant motion, and this motion cannot be controlled consciously. Therefore, in a conscious patient the eye is expected to be in motion. In general, there are two types of eye movements. One type of eye movements is called drift and consists of random and slow eye movements. Another type of eye movement is the saccade, which is a high acceleration ballistic movement that moves the eye quickly from one position to another.

When the eye is moving during the raster scanning process, many image distortions are caused, and are analogous to rolling shutter distortion in some modern digital sensors, for example those commonly used in mobile phones and portable video cameras. Eye-motion can cause compression or expansion of the image when motion is in the slow-scan direction, and shearing when motion is in the fast-scan direction. However real eye motion is typically complex and consists of random drift and saccades in multiple directions which cause complicated image distortions. In addition, saccades give very fast eye motion which can cause highly problematic distortions that often cannot be corrected, even when the exact motion of the saccade is known. A saccade can additionally cause a rapid translation of the field of view of the retina from image to image, resulting in large shifts between two neighboring images. If a saccade begins, or ends, in the middle of a scan, such distortions may change across the image, or may appear in combination.

Without any further processing, the images captured by the AO-SLO are not generally useful for doctors due to the large distortions in images that have been introduced by the eye motion. The effect of these distortions on the retinal video from the AO-SLO is to cause them to be both warped and to change location from image to image so that it is extremely difficult to see stable structures on the retina. Therefore, it is important to minimize the effect of the eye motion. One method to do this is to have the patient fixate their vision by locking their gaze at a visible marker; this reduces the wandering of the eye. However, the eye will still move even when fixated and additionally there are many patients who have poor vision and the fixation point is difficult to see or not visible at all. Also, there are automated systems which can track eye motion and compensate for some of the eye movement. However, these systems cannot compensate for all eye motion, and typically have a lag which means that there are still residual distortions that must be accounted for.

Therefore, it is desirable to perform alignment processing to reduce the effect of the eye motion and stabilize images across the captured image sequence which is robust to large and small eye motion. Alignment processing traditional consists of positioning images in the AO-SLO video sequence so that the same physical feature in one image is located at the same position in all the images of an image sequence. There are many methods to perform such alignment of AO-SLO image sequences. A typical alignment process for a sequence of AO-SLO images involves selecting a reference image from the sequence and calculating the location of image features in the reference image in the rest of the images. Once the locations of common features are known, the images can be aligned using a number of methods. One problem with this approach is that the amount of overlap between the reference image and any other image from the sequence can vary significantly, especially with rapid translations of the field of view that are commonly caused by saccades. In cases where there are substantial shifts between the images, registration performance in the non-overlapping regions is usually poor due to the lack of alignment features.

FIG. 1 shows a schematic representation of the alignment of two frames 120 and 130 with a reference frame 110. This illustration shows that, for any given pair of images from an AO-SLO sequence, there are likely to be some regions which appear in one image but not in another image. The first frame 120 has a large overlap with frame 110 and can be aligned well. However, the second frame 130 has a low overlap and there is a large area 135 for which there is no overlap with the reference frame 110. In this non-overlapping region 135 alignment information is not available, and this can lead to poor registration results. Note that the non-overlapping region 135 only contains the area which has no overlap between the reference 110 and target image 130 in an entire column. Any area where the target image 130 does not overlap some pixels of the reference image 110 but there is overlap in another part of the column is not considered to be non-overlapping. For example, the area 140 of the target frame 130 below the reference frame 110 but to the right of the non-overlap region 135 is considered to be overlapping. Given that scanning in x direction is much slower compared to scanning in y direction, the eye motion is substantially the same within each column in the image and different across columns in the image. Therefore knowledge of the eye position in the upper part of an image can be used to estimate the eye position in the lower part of an image.

SUMMARY

According to one aspect of the disclosure, there is provided a method of compensating for distortion, in a plurality of retinal image frames, as a result of eye movement, the method comprising:

(a) receiving, from the plurality of image frames, at least one reference image frame and a plurality of other image frames capturing substantially the same portion of the eye;

(b) for each image frame, in the plurality of other image frames, determining a plurality of shifts relative to the reference image frame, the shifts representing distortion within each said image frame with respect to the reference image frame;

(c) determining an initial eye movement trajectory based on at least an initial reference frame distortion and the shifts within each of said other image frames;

(d) estimating a current reference frame distortion using the initial eye movement trajectory and the plurality of shifts within each of said other image frames;

(e) estimating a current eye movement trajectory based on the estimated current reference frame distortion, and the shifts within each of said other image frames to provide a smooth transition between the other image frames in the eye movement; and (f) compensating for distortion in said frames using the current eye movement trajectory.

Preferably the method further comprises repeating steps (d) and (e) at least once to determine an iterated current eye movement trajectory.

Desirably the estimating of steps (c) and (e) is further based on predetermined dynamics of the eye.

According to another aspect there is provided a method of compensating for distortion, in a plurality of image frames, as a result of eye movement, the method comprising:

receiving, from the plurality of image frames, at least one reference image frame and a plurality of other image frames capturing substantially the same portion of the eye;

for each image frame, in the plurality of other image frames, determining a plurality of shift values relative to the reference image frame, the shift values representing distortion within each said image frame with respect to the reference image frame;

determining an individual eye movement trajectory for each other image frame and a transition between pairs of adjacent ones of the other image frames, the eye movement trajectory being based at least on the distortion within each of said other image frames determining a reference frame distortion from the transitions; and compensating for distortion in said plurality of image frames using the determined eye movement trajectories and the reference frame distortion.

Desirably the compensating comprises:

estimating a global eye movement trajectory using the determined reference frame distortion; and dewarping the plurality of images using the global eye movement trajectory.

In an advantageous implementation the estimating of the eye movement trajectory is further based on predetermined dynamics of the eye According to another aspect there is provided a method of compensating for distortion, in a plurality of image frames, as a result of eye movement, the method comprising:

receiving, from the a plurality of image frames, at least one reference image frame and a plurality of other image frames capturing substantially the same portion of the eye, the other image frames being captured sequentially and substantially continuously;

for each image frame, in the plurality of other image frames, determining a plurality of shifts within each said image frame with respect to the reference image frame;

establishing a mutual dependency between a reference frame distortion and an eye movement trajectory using predetermined dynamics of the eye and the plurality of shifts within each of said other image frames;

determining the eye movement trajectory in accordance with the established mutual dependency using the reference frame distortion, which allows for a smooth transition, in the determined eye movement trajectory, between pairs of adjacent other image frames; and compensating for distortion in said plurality of image frames using the determined eye movement trajectory.

The methods may further comprise using a smoothing spline interpolation between the plurality of shifts within each of the plurality of other image frames to determine a current eye movement trajectory.

Desirably the plurality of shifts are determined in an area of overlap between said frame and the reference frame. Preferably the compensating comprises using the determined eye movement trajectory to adjust portions of the frames outside the areas of overlap.

In specific implementations the predetermined dynamics of the eye include at least one of velocity, acceleration and speed. In others, the individual eye movement trajectory for a frame is determined by extrapolating relative shifts of two adjacent consecutive frames from the plurality of frames.

The methods may further comprise using the determined eye movement trajectory to identify a further reference frame.

In certain examples, the methods further comprise displaying at least one of the determined eye movement trajectories and the compensated sequence of eye images.

Preferably the plurality of frames is captured successively and the reference frame is selected from at least one of any of the captured frames. Advantageously the reference frame is generated by averaging multiple frames.

Other aspects are also disclosed.

BRIEF DESCRIPTION OF THE DRAWINGS

At least one embodiment of the invention will now be described with reference to the following drawings, in which.

DETAILED DESCRIPTION INCLUDING BEST MODE

Physical Implementation

Figure 16A:
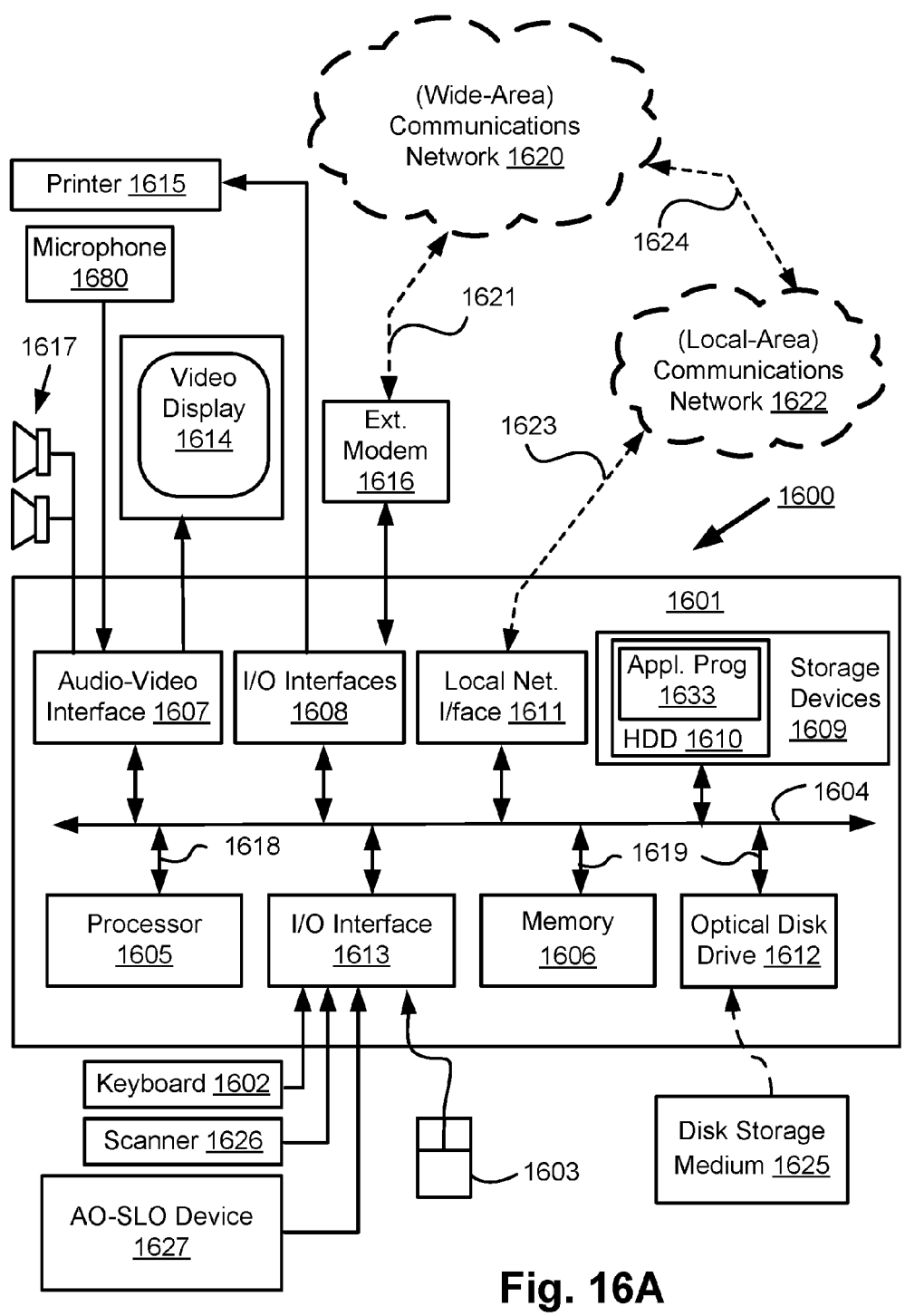
FIGS. 16A and 16B form a schematic block diagram of an AO-SLO system and general purpose computer system upon which arrangements described can be practiced.
Figure 16B:
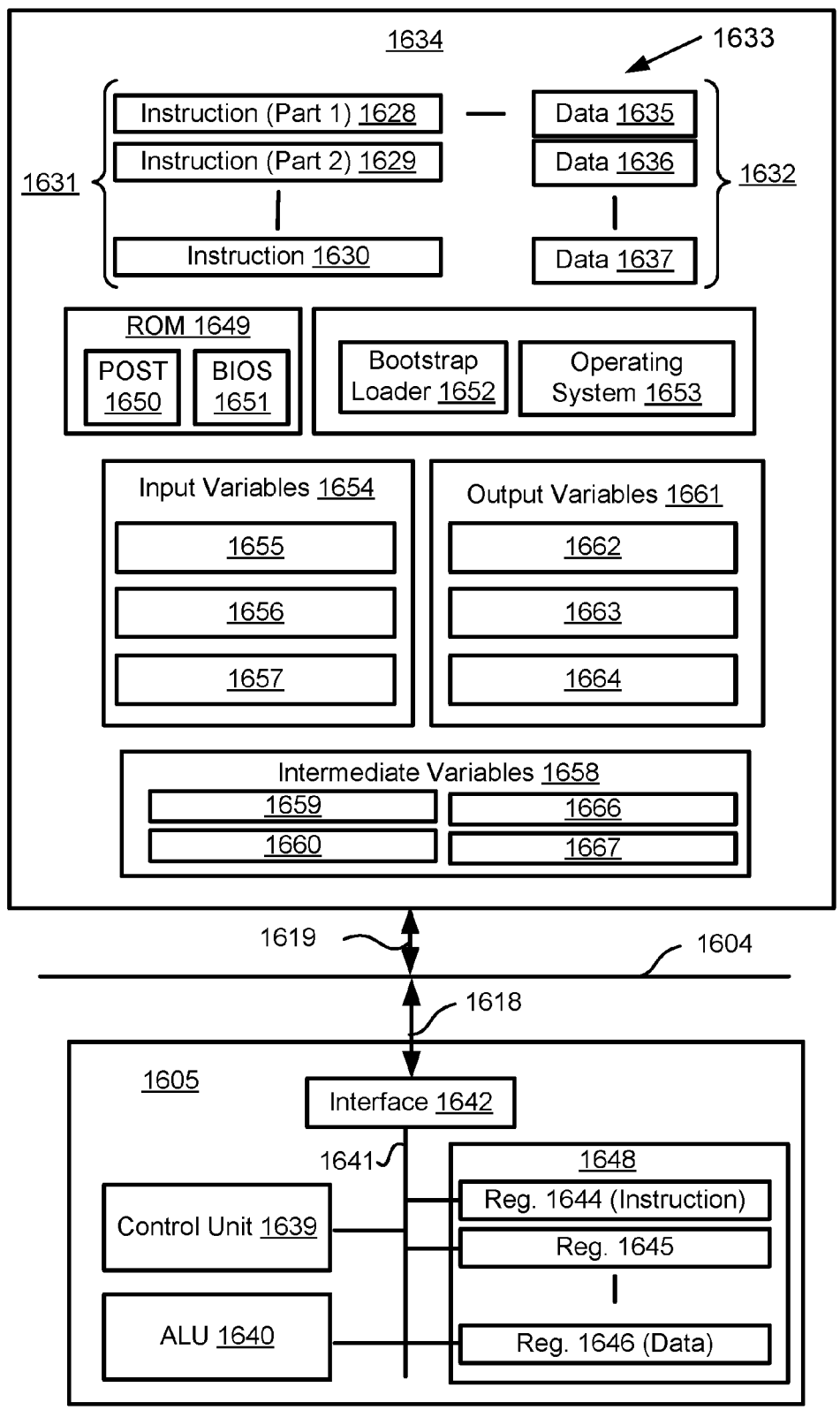

FIGS. 16A and 16B depict an AO-SLO and general-purpose computer system 1600, upon which the various arrangements described can be practiced.

As seen in FIG. 16A, the computer system 1600 includes: a computer module 1601; input devices such as a keyboard 1602, a mouse pointer device 1603, a scanner 1626, an AO-SLO device 1627, and a microphone 1680; and output devices including a printer 1615, a display device 1614 and loudspeakers 1617. With this arrangement, retinal images can be captured by the AO-SLO device 1627 and passed to the computer module 1601 for processing in accordance with the methods to be described to generate, for example, a stabilised movie demonstrating a blood flow in the eye. In some implementations, the computer device 1601 may be formed within or otherwise integrated with an AO-SLO device. In the illustrated implementation, an external Modulator-Demodulator (Modem) transceiver device 1616 may be used by the computer module 1601 for communicating to and from a communications network 1620 via a connection 1621. The communications network 1620 may be a wide-area network (WAN), such as the Internet, a cellular telecommunications network, or a private WAN. Where the connection 1621 is a telephone line, the modem 1616 may be a traditional "dial-up" modem. Alternatively, where the connection 1621 is a high capacity (e.g., cable) connection, the modem 1616 may be a broadband modem. A wireless modem may also be used for wireless connection to the communications network 1620. In this fashion, an AO-SLO device configured as part of the networks 1620 and/or 1622 may operate as a remote source of retinal data that may be transferred to the computer module 1601 for processing according to the present disclosure. Such a configuration permits so-called cloud computing implementations registration and distortion compensation of retinal images.

The computer module 1601 typically includes at least one processor unit 1605, and a memory unit 1606. For example, the memory unit 1606 may have semiconductor random access memory (RAM) and semiconductor read only memory (ROM). The computer module 1601 also includes an number of input/output (I/O) interfaces including: an audio-video interface 1607 that couples to the video display 1614, loudspeakers 1617 and microphone 1680; an I/O interface 1613 that couples to the keyboard 1602, mouse 1603, scanner 1626, AO-SLO device 1627 and optionally a joystick or other human interface device (not illustrated); and an interface 1608 for the external modem 1616 and printer 1615. In some implementations, the modem 1616 may be incorporated within the computer module 1601, for example within the interface 1608. The computer module 1601 also has a local network interface 1611, which permits coupling of the computer system 1600 via a connection 1623 to a local-area communications network 1622, known as a Local Area Network (LAN). As illustrated in FIG. 16A, the local communications network 1622 may also couple to the wide network 1620 via a connection 1624, which would typically include a so-called "firewall" device or device of similar functionality. The local network interface 1611 may comprise an Ethernet circuit card, a Bluetooth™ wireless arrangement or an IEEE 802.11 wireless arrangement; however, numerous other types of interfaces may be practiced for the interface 1611.

The I/O interfaces 1608 and 1613 may afford either or both of serial and parallel connectivity, the former typically being implemented according to the Universal Serial Bus (USB) standards and having corresponding USB connectors (not illustrated). Storage devices 1609 are provided and typically include a hard disk drive (HDD) 1610. Other storage devices such as a floppy disk drive and a magnetic tape drive (not illustrated) may also be used. An optical disk drive 1612 is typically provided to act as a non-volatile source of data. Portable memory devices, such optical disks (e.g., CD-ROM, DVD, Blu-ray Disc™), USB-RAM, portable, external hard drives, and floppy disks, for example, may be used as appropriate sources of data to the system 1600.

The components 1605 to 1613 of the computer module 1601 typically communicate via an interconnected bus 1604 and in a manner that results in a conventional mode of operation of the computer system 1600 known to those in the relevant art. For example, the processor 1605 is coupled to the system bus 1604 using a connection 1618. Likewise, the memory 1606 and optical disk drive 1612 are coupled to the system bus 1604 by connections 1619. Examples of computers on which the described arrangements can be practiced include IBM-PC's and compatibles, Sun Sparestations™, Apple Mac™ or a like computer systems.

The methods of retinal registration and distortion compensation disclosed herein may be implemented using the computer system 1600 wherein the processes of FIGS. 2 to 15, to be described, may be implemented as one or more software application programs 1633 executable within the computer system 1600. In particular, the distortion compensation methods are effected by instructions 1631 (see FIG. 16B) in the software 1633 that are executed within the computer system 1600. The software instructions 1631 may be formed as one or more code modules, each for performing one or more particular tasks. The software may also be divided into two separate parts, in which a first part and the corresponding code modules performs the distortion compensation methods and a second part and the corresponding code modules manage a user interface between the first part and the user.

The software may be stored in a computer readable medium, including the storage devices described below, for example. The software is loaded into the computer system 1600 from the computer readable medium, and then executed by the computer system 1600. A computer readable medium having such software or computer program recorded on the computer readable medium is a computer program product. The use of the computer program product in the computer system 1600 preferably effects an advantageous apparatus for retinal image registration and distortion compensation.

The software 1633 is typically stored in the HDD 1610 or the memory 1606. The software is loaded into the computer system 1600 from a computer readable medium, and executed by the computer system 1600. Thus, for example, the software 1633 may be stored on an optically readable disk storage medium (e.g., CD-ROM) 1625 that is read by the optical disk drive 1612. A computer readable medium having such software or computer program recorded on it is a computer program product. The use of the computer program product in the computer system 1600 preferably effects an apparatus for retinal image registration and distortion compensation.

In some instances, the application programs 1633 may be supplied to the user encoded on one or more CD-ROMs 1625 and read via the corresponding drive 1612, or alternatively may be read by the user from the networks 1620 or 1622. Still further, the software can also be loaded into the computer system 1600 from other computer readable media. Computer readable storage media refers to any non-transitory tangible storage medium that provides recorded instructions and/or data to the computer system 1600 for execution and/or processing. Examples of such storage media include floppy disks, magnetic tape, CD-ROM, DVD, Blu-ray Disc™, a hard disk drive, a ROM or integrated circuit, USB memory, a magneto-optical disk, or a computer readable card such as a PCMCIA card and the like, whether or not such devices are internal or external of the computer module 1601. Examples of transitory or non-tangible computer readable transmission media that may also participate in the provision of software, application programs, instructions and/or data to the computer module 1601 include radio or infra-red transmission channels as well as a network connection to another computer or networked device, and the Internet or Intranets including e-mail transmissions and information recorded on Websites and the like.

The second part of the application programs 1633 and the corresponding code modules mentioned above may be executed to implement one or more graphical user interfaces (GUIs) to be rendered or otherwise represented upon the display 1614. Through manipulation of typically the keyboard 1602 and the mouse 1603, a user of the computer system 1600 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 1617 and user voice commands input via the microphone 1680.

FIG. 16B is a detailed schematic block diagram of the processor 1605 and a "memory" 1634. The memory 1634 represents a logical aggregation of all the memory modules (including the HDD 1609 and semiconductor memory 1606) that can be accessed by the computer module 1601 in FIG. 16A.

When the computer module 1601 is initially powered up, a power-on self-test (POST) program 1650 executes. The POST program 1650 is typically stored in a ROM 1649 of the semiconductor memory 1606 of FIG. 16A. A hardware device such as the ROM 1649 storing software is sometimes referred to as firmware. The POST program 1650 examines hardware within the computer module 1601 to ensure proper functioning and typically checks the processor 1605, the memory 1634 (1609, 1606), and a basic input-output systems software (BIOS) module 1651, also typically stored in the ROM 1649, for correct operation. Once the POST program 1650 has run successfully, the BIOS 1651 activates the hard disk drive 1610 of FIG. 16A. Activation of the hard disk drive 1610 causes a bootstrap loader program 1652 that is resident on the hard disk drive 1610 to execute via the processor 1605. This loads an operating system 1653 into the RAM memory 1606, upon which the operating system 1653 commences operation. The operating system 1653 is a system level application, executable by the processor 1605, to fulfil various high level functions, including processor management, memory management, device management, storage management, software application interface, and generic user interface.

The operating system 1653 manages the memory 1634 (1609, 1606) to ensure that each process or application running on the computer module 1601 has sufficient memory in which to execute without colliding with memory allocated to another process. Furthermore, the different types of memory available in the system 1600 of FIG. 16A must be used properly so that each process can run effectively. Accordingly, the aggregated memory 1634 is not intended to illustrate how particular segments of memory are allocated (unless otherwise stated), but rather to provide a general view of the memory accessible by the computer system 1600 and how such is used.

As shown in FIG. 16B, the processor 1605 includes a number of functional modules including a control unit 1639, an arithmetic logic unit (ALU) 1640, and a local or internal memory 1648, sometimes called a cache memory. The cache memory 1648 typically includes a number of storage registers 1644-1646 in a register section. One or more internal busses 1641 functionally interconnect these functional modules. The processor 1605 typically also has one or more interfaces 1642 for communicating with external devices via the system bus 1604, using a connection 1618. The memory 1634 is coupled to the bus 1604 using a connection 1619.

The application program 1633 includes a sequence of instructions 1631 that may include conditional branch and loop instructions. The program 1633 may also include data 1632 which is used in execution of the program 1633. The instructions 1631 and the data 1632 are stored in memory locations 1628, 1629, 1630 and 1635, 1636, 1637, respectively. Depending upon the relative size of the instructions 1631 and the memory locations 1628-1630, a particular instruction may be stored in a single memory location as depicted by the instruction shown in the memory location 1630. Alternately, an instruction may be segmented into a number of parts each of which is stored in a separate memory location, as depicted by the instruction segments shown in the memory locations 1628 and 1629.

In general, the processor 1605 is given a set of instructions which are executed therein. The processor 1605 waits for a subsequent input, to which the processor 1605 reacts to by executing another set of instructions. Each input may be provided from one or more of a number of sources, including data generated by one or more of the input devices 1602, 1603, data received from an external source across one of the networks 1620, 1622, data retrieved from one of the storage devices 1606, 1609 or data retrieved from a storage medium 1625 inserted into the corresponding reader 1612, all depicted in FIG. 16A. The execution of a set of the instructions may in some cases result in output of data. Execution may also involve storing data or variables to the memory 1634.

The disclosed imaging arrangements use input variables 1654, which are stored in the memory 1634 in corresponding memory locations 1655, 1656, 1657. The imaging arrangements produce output variables 1661, which are stored in the memory 1634 in corresponding memory locations 1662, 1663, 1664. Intermediate variables 1658 may be stored in memory locations 1659, 1660, 1666 and 1667.

Referring to the processor 1605 of FIG. 16B, the registers 1644, 1645, 1646, the arithmetic logic unit (ALU) 1640, and the control unit 1639 work together to perform sequences of micro-operations needed to perform "fetch, decode, and execute" cycles for every instruction in the instruction set making up the program 1633. Each fetch, decode, and execute cycle comprises:

(i) a fetch operation, which fetches or reads an instruction 1631 from a memory location 1628, 1629, 1630;

(ii) a decode operation in which the control unit 1639 determines which instruction has been fetched; and (iii) an execute operation in which the control unit 1639 and/or the ALU 1640 execute the instruction.

Thereafter, a further fetch, decode, and execute cycle for the next instruction may be executed. Similarly, a store cycle may be performed by which the control unit 1639 stores or writes a value to a memory location 1632.

Each step or sub-process in the processes of FIGS. 2 to 15 may associated with one or more segments of the program 1633 and is performed by the register section 1644, 1645, 1646, the ALU 1640, and the control unit 1639 in the processor 1605 working together to perform the fetch, decode, and execute cycles for every instruction in the instruction set for the noted segments of the program 1633.

The methods or individual processes thereof may alternatively be implemented in dedicated hardware such as one or more integrated circuits performing the functions or sub functions of retinal registration and distortion compensation. Such dedicated hardware may include graphic processors, digital signal processors, or one or more microprocessors and associated memories.

Context

Figure 1:
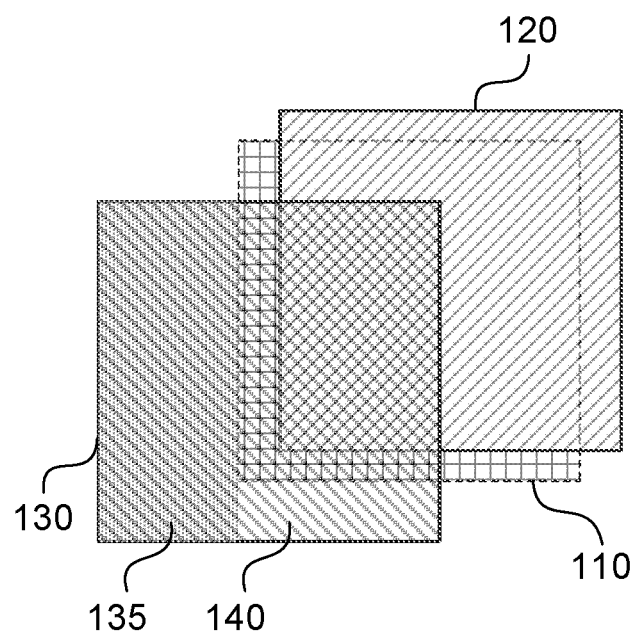
FIG. 1 is an illustration of overlapping image frames during the registration process.
Figure 2:
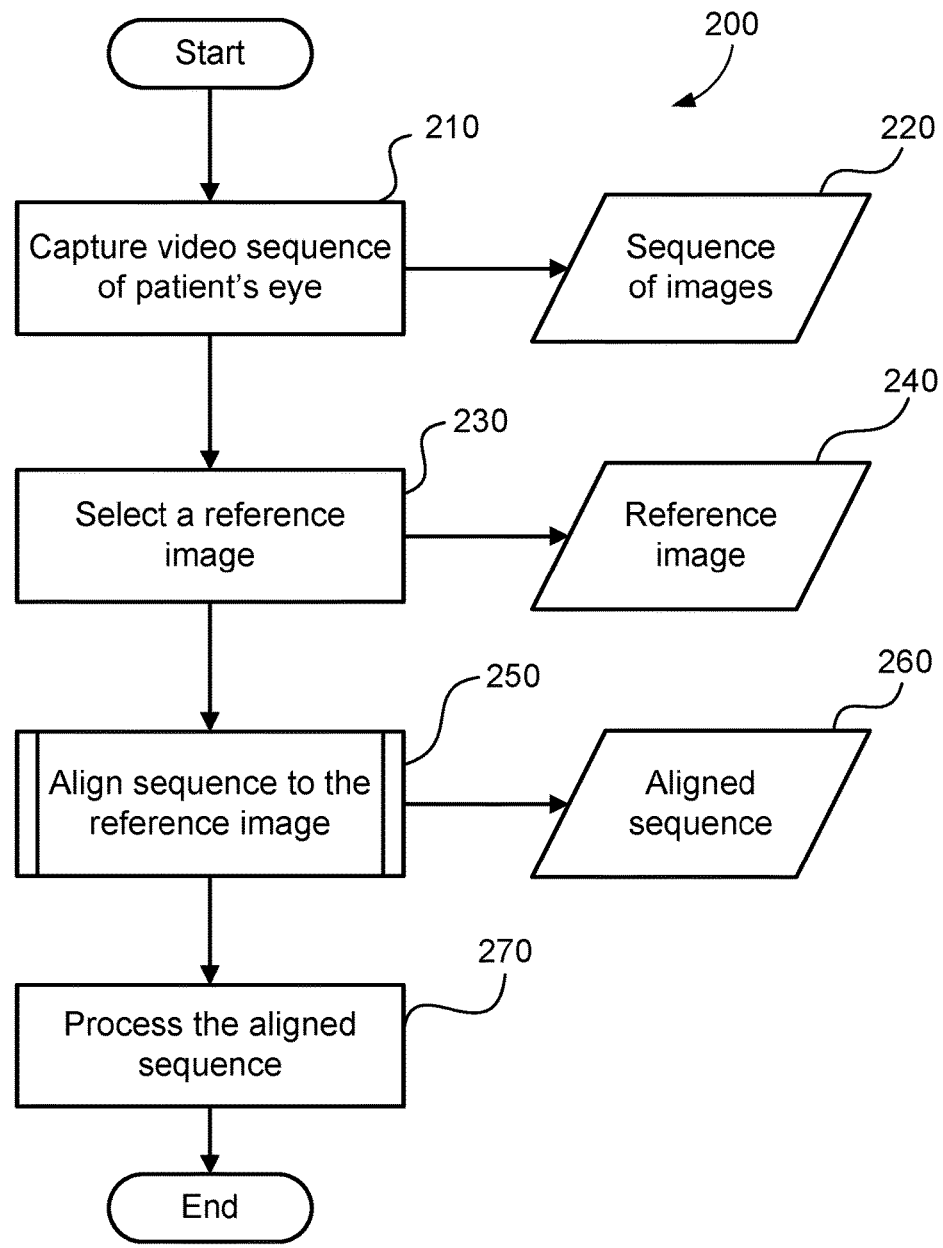
FIG. 2 is a schematic block diagram of an AO-SLO process from acquiring an image sequence from a patient's retina to processing that image sequence for diagnosis.

A process 200 for capturing and aligning retinal image sequences for diagnosis using the AO-SLO device 1627 is shown in FIG. 2.

In step 210, a patient is seated in front of the AO-SLO device 1627, and requested to look into the device at a fixation point. The AO-SLO device 1627 is then operated to capture sequentially and substantially continuously a sequence of images or frames 220 at the specific frame rate of the AO-SLO device 1627. Each image of the sequence 220 is often desired to be captured at the same position in the retina, e.g. the images represent substantially co-located areas of the retina, being portions of the eye of the patient. These areas are quite small, typically having dimensions of the order of 1 mm$^2$ to 10 mm$^2$. This can be achieved by requesting the patient fixation their gaze, or by tracking the retina and reconfiguring the optics to track a single position on the retina, or any other means.

Figure 3A:
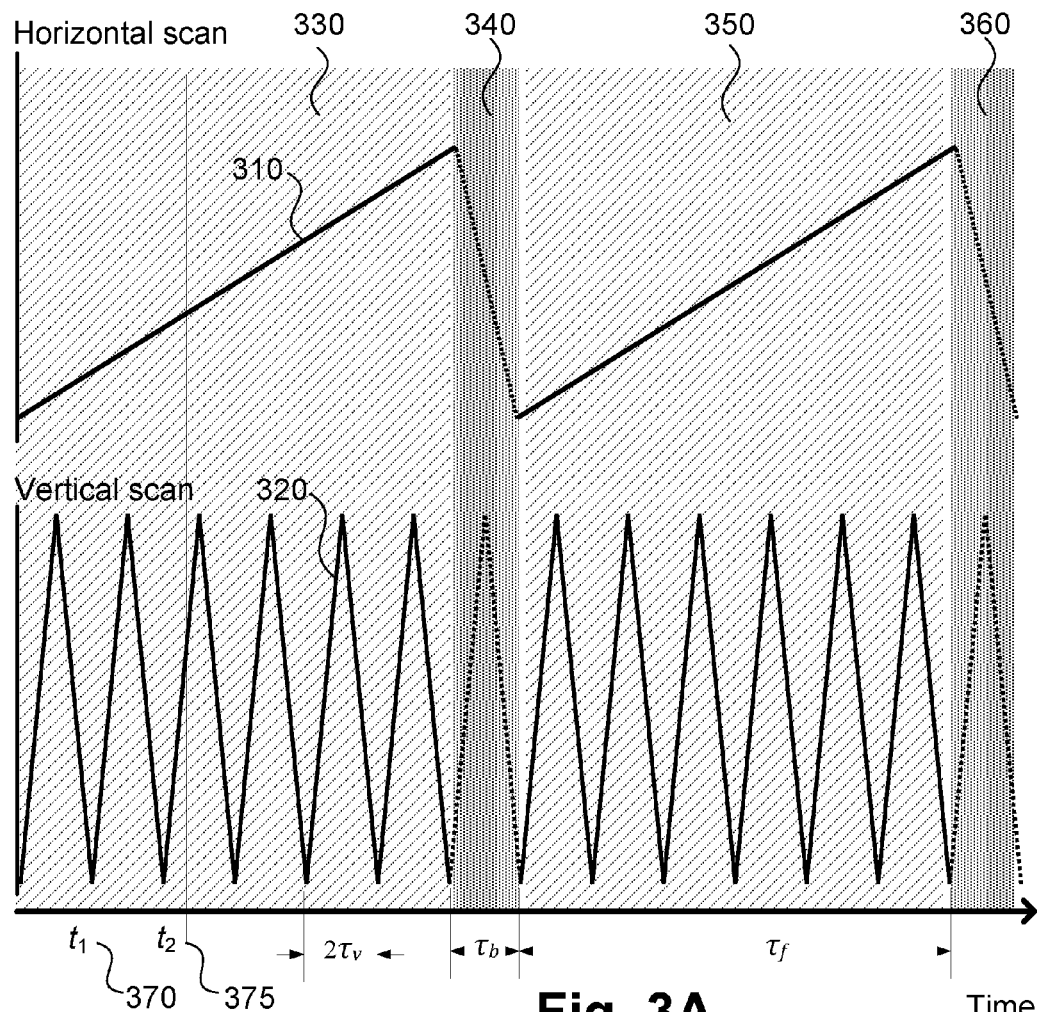
FIGS. 3A and 3B illustrate a raster scanning process over two consecutive images using an AO-SLO device and an image captured from this raster scan process.

FIG. 3A provides an illustration of a raster scanning process performed by the AO-SLO device 1627 during the image capture step 210, over two consecutive image frames. FIG. 3A shows the horizontal scan position 310 and the vertical scan position 320 of the laser as it scans a 2D area on the retina. The horizontal scan position 310 is used to drive a mirror that moves the laser beam horizontally, and the vertical scan position 320 is used to drive a resonant scanner that moves the laser beam vertically. This enables the combined vertical and horizontal signals to address the locations of points spaced throughout the area of interest. The first frame is captured during the scanning time 330, and the second frame is captured during the later time period 350. There is a delay 340 between the end of the capture of the first frame 330 and the start of the capture of the second frame 350 due to the need to return the laser to the starting position in the retina. This starting position is assumed to be the same for each frame, but could be changed to enable capturing a wider area of the retina. Each vertical scanning line consists of one scan up or down the entire scanning area and takes a time $\tau_v$, each horizontal scan takes a time $\tau_f$ which represents the time to scan the area of interest. The time for the beam to return to the start of the scanning position from the end of the scan is the beam-return time $\tau_b$. Therefore the total scanning rate is $1/(\tau_f+\tau_b)$ frames per second, and the number of vertical lines in a single frame is $N_f = \tau_f/\tau_v$.

Figure 3B:
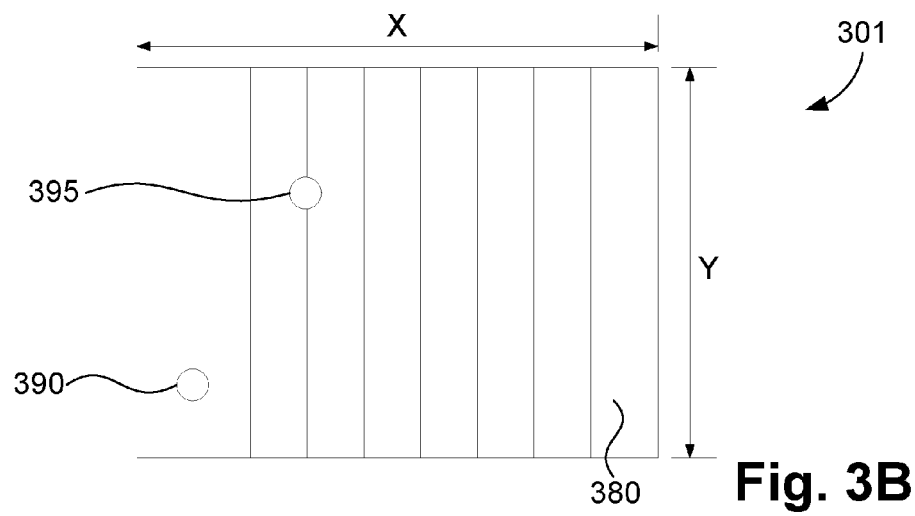

FIG. 3B shows the resulting image 301 captured from the raster scanning process. This image 301 is captured from the raster scan by an image sensor of the AO-SLO device 1627 sampling the reflected intensity at different times. Each different time typically corresponds to a different location in the retina, typically at points arranged in an equally-spaced grid. For example, a time $t_1$ in FIG. 3A corresponds to the point or location 390 in the first captured image 380, and a point at a later time $t_2$ corresponds to a different point 395 in the first captured image 380. The captured frame 380 consists of a rectangular area with dimensions X×Y in some units. Furthermore, each column of the capture image 380 is captured in a single period $\tau_v$ of the vertical raster scan 320. Therefore, assuming the vertical raster scan 320 is fast in comparison to the eye motion, each column can be considered to have been captured at the same time, dependent only on the x coordinate of the captured image 380, as given by Equation [1], $$t(x) = t_0 + \frac{x}{X}\tau_f \quad [1]$$

where $t_0$ is the time when the scanning of the captured image starts, x is the x location of the captured image 380 as counted in the direction of the slow scan, and X is the total number of columns of the captured image 380.

Figure 4A:
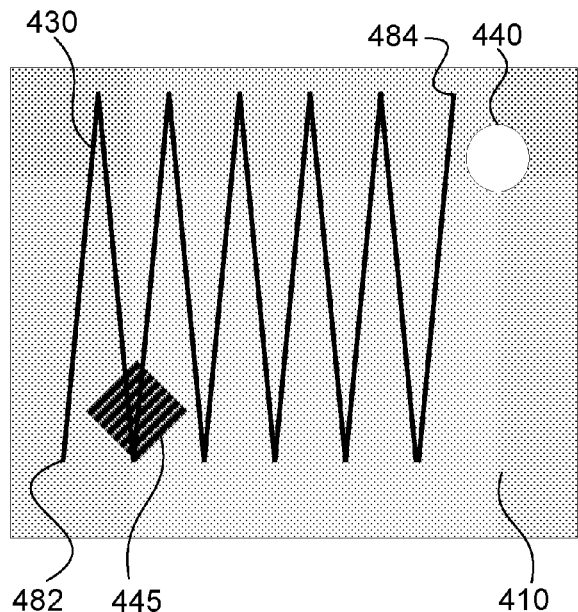
FIGS. 4A to 4D illustrate a raster scanning process occurring both with and without movement of the retina, and the effect on the captured images.
Figure 4B:
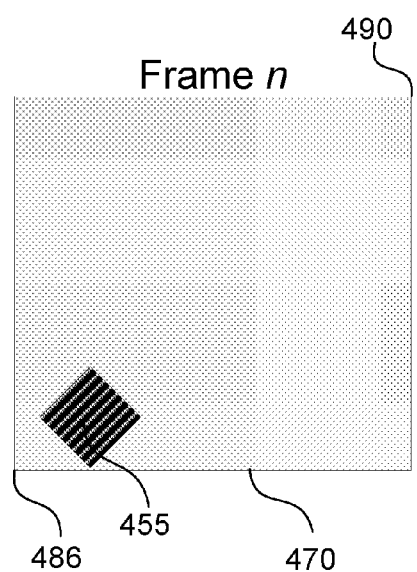
Figure 4C:
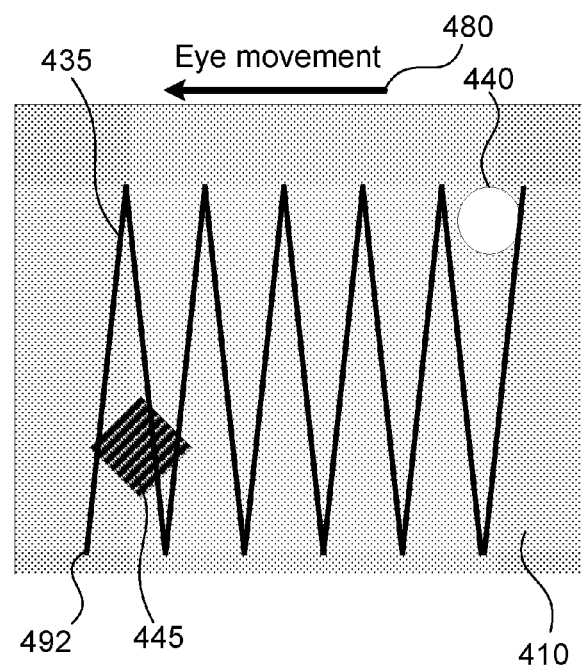
Figure 4D:
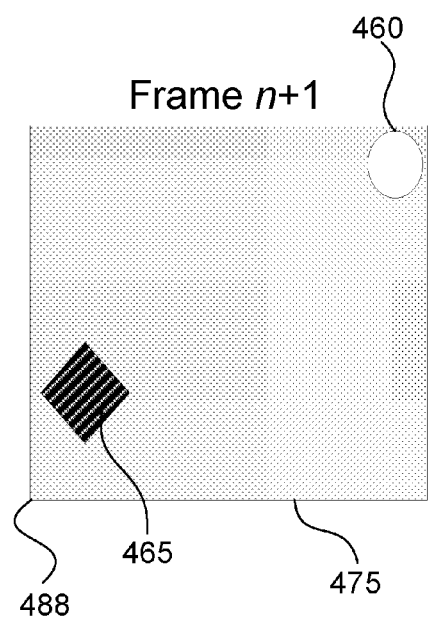

FIGS. 4A to 4D show the effect of eye motion on the capture of an area on the retina 410 that contains, for example, two features of interest 440 and 445. FIG. 4B shows a frame n which is captured when the retina is in not in motion. The corresponding raster scan 430 of FIG. 4A traces an area on the retinal surface that covers one feature of interest 445. The captured image formed by the raster scan 430 is represented by image 470 and contains an image of the feature of interest 445 located at position 455 in the captured image 470. FIG. 4D shows a frame captured for the succeeding frame n+1 where the retina has moved vertically and horizontally in the time between frame captures, and continues to move horizontally during the frame capture as indicated by the arrow 480. The corresponding raster scan 435 of frame n+1 typically starts at a different position, being position 492, in the retina 410 because of the motion before the start of the capture. This causes the feature of interest 445 to be located in a different position 465 in the second captured image 475 as compared to the same feature position 455 in the previous captured image 470. The continual motion during capture causes the raster scan 435 of frame n+1 to cover a larger horizontal area of the retina 410 than the raster scan 430 of frame n. This, in turn, causes the other feature of interest 440 to be contained in the raster scan area and to appear in the captured image 475 as given by the image feature 460. Furthermore, the horizontal motion of the retina during scanning distorts the shape of the captured image 475 so that the image feature 465 is horizontally compressed as compared to the image feature 455 in the previous captured image 470 of frame n. From this it will be appreciated that because of the nature of AO-SLO scanning, horizontal (x-direction) and vertical (y-direction) distortions do not change within a single column of the scanned image, assuming no rotations of the eye. Therefore, the distortions are completely described by the position in the x direction of the image. This observation, contributes to the predetermined dynamics of the eye such that eye position is a vector that only changes in the x-direction of the image.

Returning to FIG. 2, when a sequence of images, for example the sequence 220, has been gathered, a reference image is selected, in step 230. This reference image is typically chosen to have high quality and to provide an anchor position to which other images in the sequence can be aligned. The quality of the image is a combination of several characteristics. Firstly, a reference image should have good lighting and contrast characteristics in which the image was gathered through a clear part of the lens and without occlusion by eyelashes or misplacement by the patient of their pupil. Secondly, a reference images should have low spatial distortion, which is desirable for diagnostic purposes, but also because low distortion is likely to result in higher-quality measurement of spatial distortion against other images in the image sequence. Thirdly, a reference image should be chosen to be well-positioned spatially within the complete set of images so that as many images as possible can be aligned to it. Selection of the reference image may be manual or automated. Further, the sequence of image frames is captured without imposing constraints for the reference frame to be captured successively in time with other frames in the sequence of frames, while frames in the sequence of frames are being captured successively. In a specific implementation, the reference frame may be generated by averaging multiples ones of other image frames from the captured sequence.

After being selected, the reference image 240 is used in combination with the original sequence 220 in step 250 to produce an aligned sequence 260. This aligned sequence 260 is formed of the original image sequence 220 processed so that the same physical features are in the same location across all images in the sequence. This requires both shifting the individual images of the sequence 220 so that the offset between frames caused by the eye motion is removed, and also dewarping the images of the sequence 220 so that the distortions caused to the image features within the frame are compensated for. The aligned sequence 260 can then been viewed as a stabilized and dewarped version of the origin capture of the retina and can be viewed directly by doctors as a video for diagnosis, or subjected to further application-specific processing in step 270.

The alignment process, 250, is based on a pair-wise registration operation between the reference image 240 and a target image selected from the remaining images of the original sequence 220. Each pair-wise operation is independent of the others, and thus the alignment performance of one target image has no bearing on the alignment performance of another target image. The alignment process 250 begins by iterating through all of the target images (i.e. the original sequence 220 without the reference image 240). A patch-based registration method is applied to the reference image 240 and the selected target image, in which measurements are performed at small patches located throughout the image. Selection of patch locations can be based on strong alignment features or a regular grid, depending on the expected features and their density within the images. The patch measurements can consist of measuring the relative shift between two patches, or optionally higher order information: for example, measuring an affine distortion between two patches. The patch measurements are then used to estimate a mapping, which may be represented by a coordinate transformation, between the reference image 140 and the selected target image. This co-ordinate transform can be a linear transformation, such as an affine transform, or more commonly a non-linear transform. After iterating through all the target images, the result is an aligned sequence 260.

As shown in FIG. 2, and discussed previously, the ability to accurately align a given target image to the reference image 240 is limited by how much the pair of images being aligned overlap. A part of the alignment process is to determine what information to use to estimate the alignment information in the non-overlapping regions. One approach to generate mapping information in non-overlapping regions is to perform extrapolation based on measurements made in the overlapping regions. However, when a captured image is affected by a saccade, extrapolation generally produces significant mapping errors in the aligned sequence 260.

Using this aligned sequence 260, further processing occurs in step 270, such as averaging the aligned images to produce a de-noised image in which photoreceptors can be mapped and counted, or a video sequence in which blood flow can be analyzed, or any of many other investigative techniques.

Overview

The present disclosure seeks to address the problems given in the preceding section by determining a relationship between neighboring images in the original sequence 220 in order to minimize registration errors in non-overlapping regions of the target images.

This is accomplished by first noting that a substantial reason for the poor registration in non-overlapping regions is due to the extrapolation of measurements from overlapping regions. If measurements were available beyond the edge of the frame, these errors could be reduced. Secondly, assuming that the eye motion is responsible for all distortions in the captured images, then recovering the eye motion is equivalent to the process of determining the distortions in the images. Additionally the eye motion is constrained to a certain maximum acceleration by the physical considerations of the eye itself. Acceleration of the eye can also be large, as is the case in saccades, but for drift motion acceleration is much smaller. These dynamic properties of the eye are well understood and thus represent predetermined quantities that can be drawn upon to provide for distortion compensation. Therefore, it is valid to assume that the eye moves in a continuous manner during the scanning time, this including the time during capture of an image and also the time between captures of one frame to the next. The arrangements presently disclosed seek to use the knowledge of the predetermined dynamics of the eye and that the eye motion is continuous between frames to convert the high-error extrapolation of measurements in non-overlapping areas to an interpolation of measurements across all frames, thus reducing the errors in these regions.

Figure 5:
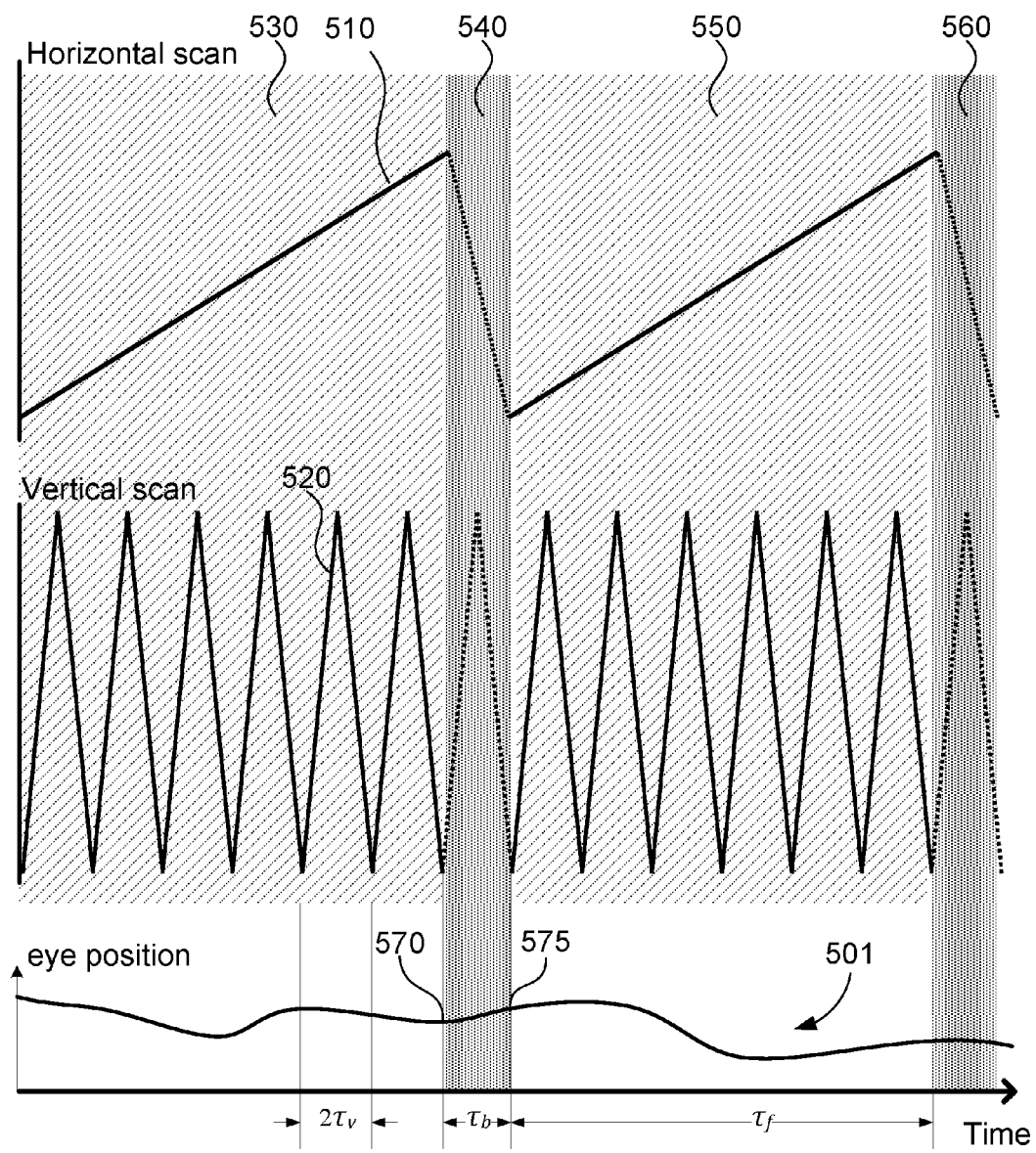
FIG. 5 is an illustration of a raster scanning process over two consecutive images and the relationship to an example eye position over time.

That is, the position of the eye at the end of one image in the sequence 220 is connected to the position of the eye at the beginning of the next image in the sequence 220. FIG. 5 provides an illustration of eye movement continuity over the duration of the scanning process. Depicted in FIG. 5 is the raster scan timeline from FIG. 3A, together with a graph 501 showing a corresponding eye position, for example the horizontal position of the eye, during the scanning of the eye. As the scanning device traverses the scanning area, the eye moves constantly as indicated by the eye movement position graph 501. The eye position is continuous in time as has been discussed earlier. This continuity of motion implies that the eye position at the end of the scan period 570 for the first frame 530 and the beginning of the scan period 575 of the second frame 550 will be close and only differs by the distance the eye has moved during the banking time 540 where the scanning laser returns to the start of the scanning area.

FIGS. 4B and 4D show the consequences on the captured image of this continuity. As previously described, FIGS. 4B and 4D show two successive frames in an AO-SLO sequence. In the first frame, FIG. 4A shows an area of the retina 410 is scanned by a raster scan 430 starting from the point 482 and finishing at the point 484. The corresponding captured image 470 is formed from left to right as the scan 430 traverses the path. Therefore the lower-left corner 486 of the captured image 470 corresponds to the location 482 on the retina, and the upper-right corner 490 of the captured image 470 corresponds to the location 484 on the retina. The capture of the second frame is shown in FIG. 4C. The area of the retina covered by the raster scan 435 is no longer the same as the one covered by raster scan 430 because of eye movements that occurred during the scanning of the first frame and in the beam-return time between frames. Again the lower-left corner 488 of the second captured image 475 corresponds to the scanning location 492 at the start of the raster scan 435. Due to the continuity of eye motion discussed in the previous paragraph, it is possible to estimate the position of the retina at the time that the bottom-left corner of image 488 is captured based on the position of the retina at the time that the top-right corner of image 490 was captured. This implies that eye movement continuity can be used to minimize registration errors in regions near image borders, where non-overlapping with the reference image tends to occur, by interpolating eye positions across image borders.

Figure 6:
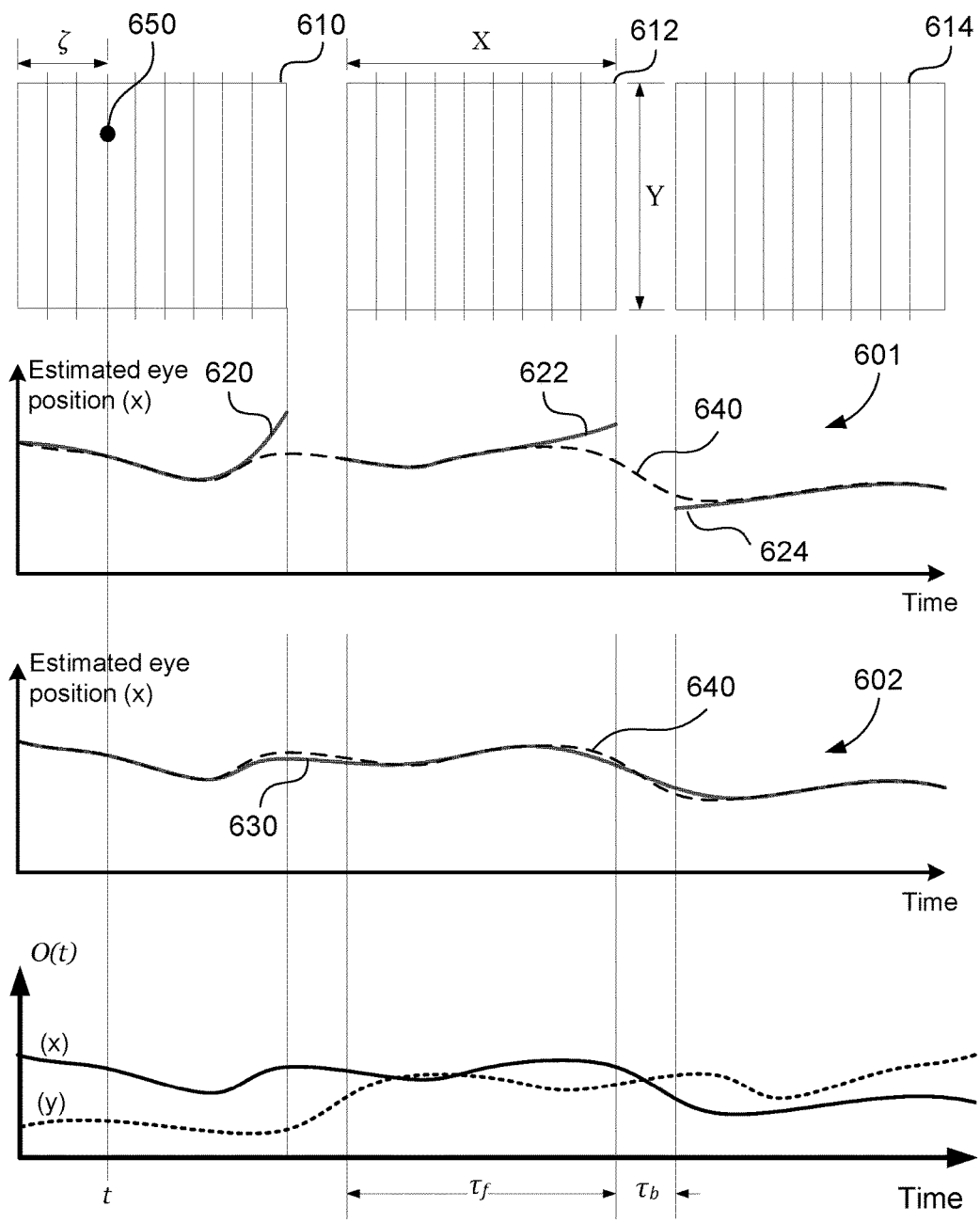
FIG. 6 is an illustration of the estimated eye position for a series of three consecutive captures images.

The use of eye movement continuity for improving registration of AO-SLO images is illustrated in FIG. 6, which shows three target AO-SLO images 610, 612, and 614 together with two eye position graphs for the x-direction, 601 and 602, showing estimated eye positions without and with eye movement continuity applied, respectively. In this example it may be assumed that the three target AO-SLO images are aligned to an undistorted reference image.

Graph 601 shows three independently estimated eye position curves 620, 622, and 624, corresponding to the three AO-SLO capture images 610, 612, and 614, respectively. These independent alignment curves give the relative position in the frame corresponding to a scanning time relative to the reference image. Also, shown in graph 601 is the true eye position curve 640. The graph 601 can be calculated using measurements at patches within the overlap region of images 610, 612, and 614 with the reference image to estimate the eye position. Using an undistorted reference image the resulting estimated eye position curves 620, 622, and 640 are close to the true eye position curve 640 across the overlap regions of the respective images. However, the estimated eye position curve 620 deviates significantly from the true eye position curve 640 in the non-overlapping region along the right border of image 610. This is because no comparison between the captured image 610 and the reference image are available in this region. Similarly, estimated eye position curves 622 and 624 are inaccurate in sections corresponding to their non-overlapping regions.

In contrast, graph 602 is a single curve spanning across the entire duration of an AO-SLO sequence. Graph 602 shows an eye position curve 630 that is estimated using all relative position measurements between the three images 610, 612, and 614 and the reference frame. Even though there is a large non-overlapping region between captured image 610 and the reference image, the application of eye movement continuity has allowed eye positions even in this non-overlapping region to be estimated by interpolating the eye positions measurements made in both images 610 and 612. As a result, the estimated eye position curve 630 is a more accurate and complete approximation of the true eye position curve 640 than the combined graph of individual estimated eye position curves 620, 622 and 624.

The final component of FIG. 6 shows the overall estimated eye position O(t) for the respective (x) and (y) directions, where the x-curve corresponds to the curve 602 and the y-curve is derived separately but in similar fashion (not otherwise illustrated).

Interpolation of eye positions based on eye movement continuity is an effective technique for minimizing registration errors across a sequence of images. However, this technique can only be applied directly if the reference image is an undistorted image of the retina. Using a reference image that is distorted, the calculation of the relative position between different parts of the target frames and the reference frame will not correspond directly to the measurement of the eye motion and will therefore not be continuous. Furthermore, as the eye is in continual motion obtaining an undistorted reference image is difficult. In particular, when a reference image is chosen from the original sequence of images 220 captured by the AO-SLO 1627 in step 230 of process 200, all frames of the input sequence of images 220 are likely to have some level of distortion. Therefore, as a result the estimated relative positions in process 200 will not be continuous across the frame boundaries. In order to overcome this problem, the reference image distortion must be estimated during eye position estimation.

Figure 7A:
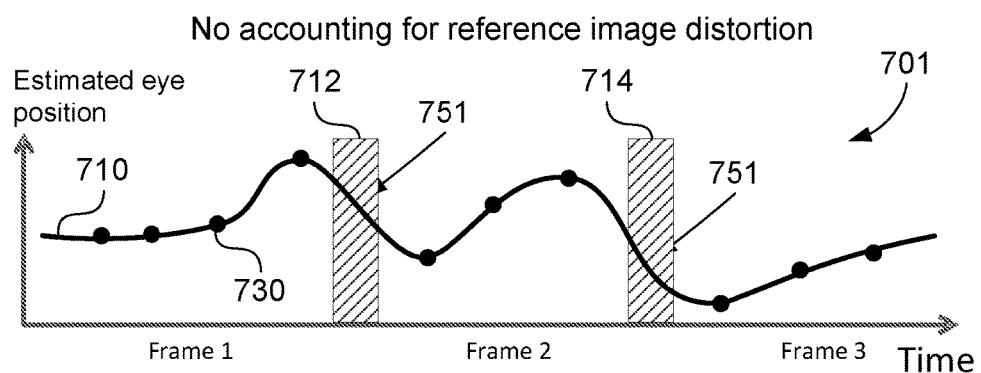
FIGS. 7A and 7B illustrate interpolation of the estimated eye position with and without reference image distortion.
Figure 7B:
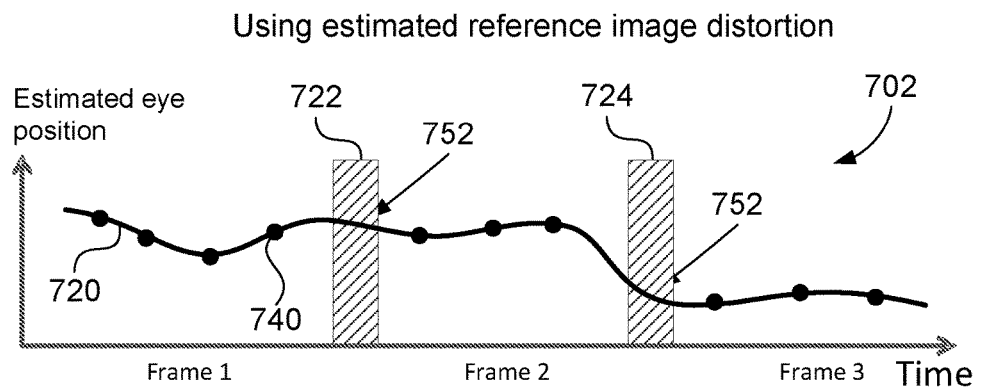

In order to estimate the distortion present on the reference image reliance is made on the observation that in the presence of reference frame distortion, the curve between the last measurement in frame n and the first measurement in frame n+1 will, in general, be less smooth than if there were no reference frame distortion. Therefore, the reference frame distortion can be estimated during eye position estimation by finding the reference frame distortion which gives a smooth curve between measurements in consecutive frames for all frames in the captured sequence 220. FIGS. 7A and 7B provide an illustration of the effect of estimating the reference frame distortion on the interpolation of the relative position measurements. Depicted in FIGS. 7A and 7B are two graphs 701 and 702 respectively, corresponding to eye position curves, 710 and 720, estimated without and with reference image distortion estimation. Graph 701 shows that with a distorted reference image, and not accounting for this distortion, there is a relatively large magnitude gradient 751 in the inter-frame periods 712 and 714 between successive images in the interpolated eye position curve 710. Graph 702 shows that when the reference image distortion is accounted for, there is a relatively smaller magnitude gradient 752 in the inter-frame periods 722 and 724 between two images in the interpolated eye position curve 720. Accordingly, using an estimate of the reference image distortion, the magnitude of the gradient of the change in eye position during the inter-frame periods is reduced, thereby providing for an improved estimate of eye position.

To mathematically express the preceding observations, the underlying eye position can be expressed as a vector, $o(t)=[o_x(t), o_y(t)]^T$, where $o_x(t)$ is the horizontal position of the retina at time t relative to some default position at time $t_0$, and $o_y(t)$ is the vertical position of the retina at time t relative to another default position at time $t_0$. It is assumed that retina only moves in x and y and does not rotate: this assumption is typically the case with most eye movements, as rotational movements of the eyeball are rare.

Recalling from FIG. 3 in Equation [1] that the time of capture of any point can be approximately calculated using only the x coordinate in the captured image, the time of capture of a pixel in column x of the nth captured image frame, for example the pixel 650 of FIG. 6, is given by Equation [2], $$t_n(x) = t_0 + \frac{\tau_f}{X}x + n\tau_T, \qquad [2]$$

where $\tau_T=(\tau_f+\tau_b)$ is the total time from the start of the capture of one frame to the start of capture of the next frame, $t_0$ is the time when the scanning of the captured image starts, and X is the total number of columns of the captured image.

The underlying eye position can therefore be written as a function of the pixel column number ζ (as seen in FIG. 6 for the pixel 650) and the frame number of the captured image sequence n. Now a scaled eye position õ is introduced which is the eye position scaled to be in the same coordinate system as the captured images, as given by Equation [3], $$o(t_n(x))=S_p õ(x+nX_T), \qquad [3]$$

where õ(x) is the eye motion function rescaled such that it is a function of the pixel column number of the raster scanning process, the scaling factor $S_p$ is such that õ is in the coordinate space of the captured image, and $X_T$ is the pixel-scaled frame capture time, as given in Equation [4], $$X_T = \frac{\tau_T}{\tau_f}X, \qquad [4]$$

Therefore, assuming the physical scan size of the scanning area in the retina is given by $(R_x, R_y)$ the scaling factor is given by Equation [5].

$$S_p = \begin{bmatrix} X/R_x & 0 \\ 0 & Y/R_y \end{bmatrix}. \qquad [5]$$

Interpolation of the Offset Measurements

Traditional approaches make use of a low-resolution estimate of the distortion on the image which is formed by interpolating a single estimate of eye position per frame. Assuming that it was possible to measure the offset between an undistorted reference image and a target image in the sequence of successive images 220 at multiple locations throughout each reference frame, it is possible to create a higher-resolution estimate of the scaled eye position and hence the (higher-resolution) distortion on the captured images by interpolating the known offset measurements. This is achieved in the described implementations, in the manner seen in FIGS. 7A and 7B where multiple estimates, and preferably at least 3 estimates, of position are obtained for each frame.

Figure 8:
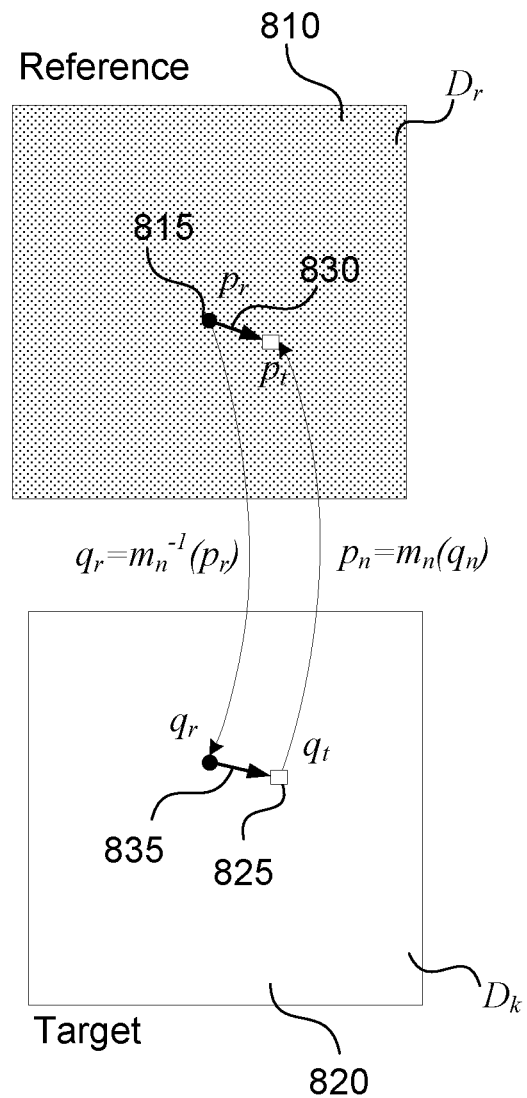
FIG. 8 is an illustration of the relationship between the geometry of two images related by a coordinate transform.

Referring to FIG. 8, a nonlinear mapping $m_n$ exists between the nth target frame 820 and the reference frame 810. Using this mapping it is possible to calculate the corresponding location $p_r$ in the reference frame 810 of a point $q_t$ in the target frame 820 as given by Equation [6].

$$p_r=m_n(q_t), \qquad [6]$$

Equation [6] is the forward mapping of a point from the reference space to the target space. There also exists an inverse mapping $m_n^{-1}$ between the reference frame 810 and the nth target frame 820 that maps the corresponding location $q_r$ in the target frame 820 of a point $p_r$ in the reference image 820 as given by Equation [7].

$$q_r=m_n^{-1}(p_r), \qquad [7]$$

When registering the target frame 820 to the reference frame 810, measurement are made of the offset between a local feature 815 in the reference image to a local feature 825 in the target image. Now considering two corresponding features, one reference image feature 815 and one target image feature 825, it is possible to calculate the offset 830 between these two features in the reference image coordinate space given by Equation [8].

$$s_r=p_t-p_r=m_n(q_t)-p_r. \qquad [8]$$

Similarly, the offset 835 in the target image coordinate space given by Equation [9].

$$s_t=q_t-q_r=q_t-m_n^{-1}(p_r). \qquad [9]$$

However, measurements of this shift are typically calculated using information from both images and cannot be considered to be measurements in either the reference or target space. Therefore, an averaged shift can be defined which can be used to enhance the accuracy of the mapping calculation without knowledge of the local scale distortions near the measurement points. Firstly, from Equations [8] and [9] the relationship of Equation [10] can be derived.

$$m_n(q_t-s_t)=m_n(q_t)-s_r=p_r. \qquad [10]$$

Equation [9] may be manipulated by taking a Taylor series expansion about $q_t$ and defining an average shift as $$s=[J(q_t)+I]^{-1}\cdot[J(q_t)\cdot s_t+s_r]$$

where $J(q_t)$ is the Jacobian matrix of the mapping $m_n(q)$ at a point $q_t$, I is the identity matrix, and $s_t$ and $s_r$ are the true shifts measured in target and reference spaces.

The Jacobian matrix $J(q_t)$ measures the local relative affine distortion between target and reference images close to the point $q_r$. When this relative affine distortion is small then the shifts measured in both target and reference space are similar, and the relation between the shift and the nonlinear mapping can be represented as shown by Equation [11], $$m_n\left(q_t - \frac{s}{2}\right) \simeq p_r + \frac{s}{2},\qquad [11]$$

where s is the shift between the target image local area 825 and reference image local area 815.

It is now assumed that in the absence of eye movement the coordinate mapping between reference and target frames is the identity. Therefore, in the case where there is eye movement, a change in the eye position while the target frame is being scanned will lead to a shift in the mapping between the target and the reference equal to the scaled eye position at the point in time that the position in the target frame is being scanned. Therefore, using Eqns. [3] and [6] the relation between the coordinate mapping and the scaled eye position can be expressed by Equation [12], $$m_n(q_t) - q_t = \tilde{o}(x + nX_T). \qquad [12]$$

where $q_t = [x,y]^T$ is the coordinate in the target image, $\tilde{o}(x+nX_T)$ is the scaled eye position at column x in frame n. The coordinate mapping $m_n(q_t)$ can be calculated across the entire frame by assuming the following: firstly, that the columns of the captured image all have the same mapping as the scan period which is too small for the eye position to change with any significance across the column; and secondly that the eye motion has a limited maximum acceleration and therefore the eye position changes smoothly with time. The calculation proceeds by noting that the mapping function $m_n$ is now a vector function of a single variable, the column number given by the variable x.

Taking a number of shift measurements $s_k$ between the target and reference images at positions $p_k$ in the reference image and $q_k$ in the target image, where $k \in \{0, 1, \ldots, K-1\}$ and K is the number of shift measurements taken, it is therefore desired to obtain an estimated coordinate mapping $\tilde{m}_n$ that is the solution to the constrained optimization problem given by Equation [13], $$\min_{m_n} \sum_{k=0}^{K-1} g\left(\left\|m_n\left(q_k - \frac{s_k}{2}\right) - p_k - \frac{s_k}{2}\right\|\right) + \lambda \int_0^L \left\|\frac{d^2 m_n(q)}{dx^2}\right\|^2 dx \qquad [13]$$

where $\lambda$ is a regularization parameter to ensure the underlying eye motion is smooth and the function $g(\cdot)$ is an error function which can be chosen to be the least-squares error function $g(l) = \frac{1}{2} l^2$ or alternatively can be an M-estimator weighting function to increase the robustness of the estimate to outliers.

A typical robust estimation function that can be used is the bi-weight function, given by Equation [14], $$g(y) = \begin{cases} \frac{\mu^2}{6}\left\{1 - \left[1 - \left(\frac{y}{\mu}\right)^2\right]^3\right\} & |y| < \mu \\ \frac{\mu^2}{6} & |y| > \mu \end{cases}, \qquad [14]$$

where the parameter $\mu$ gives the expected range of data inliers.

Note that the acceleration of the eye is the second derivative of the eye position and is proportional to the second derivative of the coordinate mapping $m_n(q)$. Therefore it can be seen that Equation [13] limits the root mean square (RMS) acceleration across the trajectory of the eye motion. Other limits to the acceleration can be considered, such as the minimum of the maximum acceleration; however, these are typically much less computationally efficient to solve and do not give large differences in the solution for the majority of cases.

Figure 9:
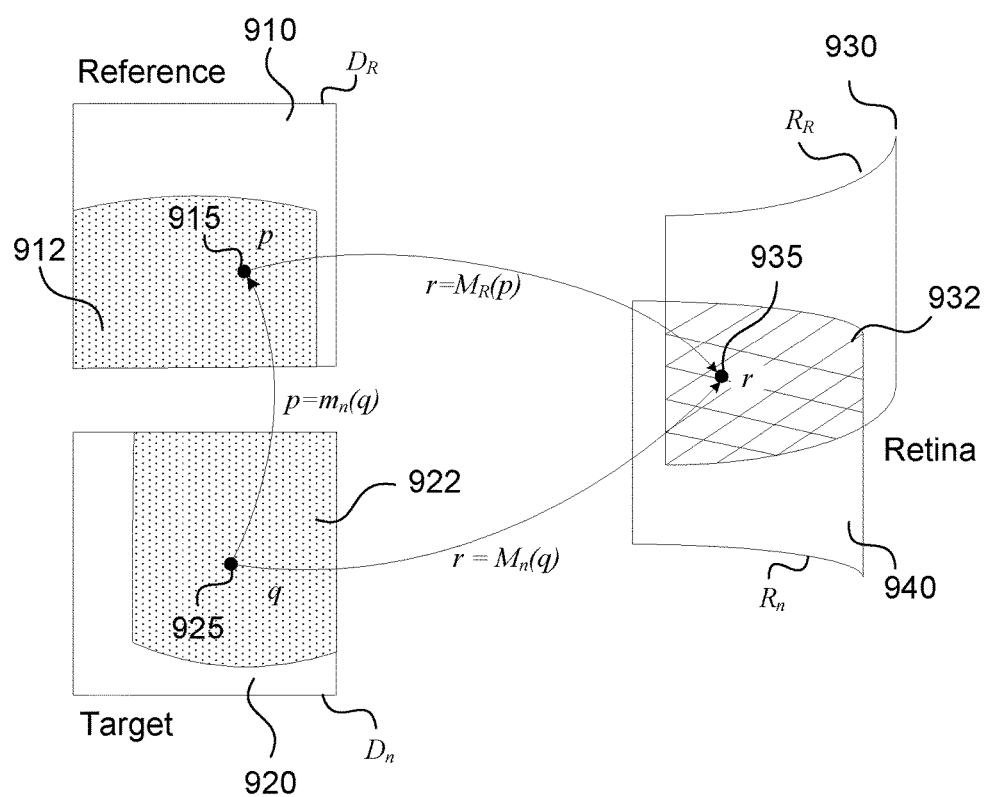
FIG. 9 is an illustration of the relationship between the geometry of two images and the retinal surface related by three coordinate transforms.

Calculation of the Eye Position and Reference Frame Mapping from Relative Offset Measurements In the formulation of Equation [13] it has been assumed that the reference frame is undistorted and the coordinate mappings are determined relative to this undistorted reference. FIG. 9 is an illustration of the mappings between distorted reference image, target image, and ground-truth retina coordinate spaces. Depicted in FIG. 9 are a reference image 910, a target image 920, a transformed reference image 930, and a transformed target image 940. The reference image 910, consisting of a number of pixel locations, represents the domain $D_R$ of an absolute mapping function $M_R$, which transforms the coordinates of the reference image domain 910 to the range $R_R$, shown as the transformed reference image 930, in the ground-truth retina coordinate space. Similarly, the target image 920 represents the domain $D_n$ of a second absolute mapping function $M_n$, which transforms the coordinates of the target image coordinate space 920 to the range $R_n$, shown as the transformed target image 940, in the ground-truth retina coordinate space. The absolute mapping function $M_R$ maps a given point p 915 in the reference image 910, to a point r 935 in the range $R_R$, and is given mathematically by Equation [15].

$$r = M_R(p). \qquad [15]$$

Additionally, the absolute mapping function $M_n$ maps a given point q 925 in the target image 920, to the same point r 935 in the range $R_n$, and is given mathematically by Equation [16].

$$r = M_n(q). \qquad [16]$$

Therefore, the relative mapping between points in the reference image 910 and the target image 920 in an area of overlap between the images is defined by the absolute mapping functions of the reference frame to the ground-truth retina space (930) and the target frame to the ground-truth retina space $M_r$ and $M_n$ (940). As seen in FIG. 9, the area of overlap is represented for each of the respective source images, being area 912 for the reference image 910, an area 922 for the target image 920, and an area 932 for the transformed images 930 and 940. As such, subject to the relevant transforms, each of the areas 912, 922 and 932 overlap. Additionally, it will be appreciated that for this relationship to be valid the point r 935 must be in the intersection of the ranges of the mapping functions $R_n$ and $R_R$, $r \in R_n \cap R_R$. This produces a relative mapping function between the target image coordinate space and reference image coordinate space written as $m_n$ and given by Equation [17].

$$p = m_n(q). \qquad [17]$$

Using this notation, the relative mapping from a point in the target image coordinate space 925 to a point in the reference image coordinate space 915 can be defined as the composition of the forward absolute target-to-retina coordinate mapping from the point in the target image coordinate space 925 to a point in the retina coordinate space 935 with the inverse relative reference-to-retina coordinate mapping between the point in the retina 935 to a point in the reference image coordinate space 915, as expressed by Equation [18], $$p = m_n(q) = M_R^{-1} \circ M_n(q), \quad [18]$$

where the notation $f \circ g$ indicates the composition of the function $f$ with the function $g$.

Now using Equation [11] the relationship between the absolute mappings for the reference image and the target image and the measured relative shift between target and reference image at locations $q_t$ in the target image and $p_r$ in the reference image can be written as Equation [19].

$$M_R^{-1} \cdot M_n\left(q_t - \frac{s}{2}\right) \simeq p_r + \frac{s}{2}. \quad [19]$$

Then the optimization problem of Equation [13] can be written for the absolute mapping function $M_n$ assuming a known $M_R$ as given by Equation [20].

$$\min_{M_n} \sum_{k=0}^{K-1} g\left(\left\|M_R^{-1} \cdot M_n\left(q_k - \frac{s_k}{2}\right) - p_k - \frac{s_k}{2}\right\|\right) + \lambda \int_0^L \left\|\frac{d^2 M_n(q)}{dx^2}\right\|^2 dx. \quad [20]$$

To utilize the knowledge that the eye motion is continuous from frame n to frame n+1, it is noted that the relation between the absolute coordinate mapping from the target frame to the retinal coordinate frame is proportional to the scaled eye position and therefore they are related by Equation [21].

$$M_n(q_t) - q_t = \tilde{o}(x + nX_T). \quad [21]$$

Therefore, the minimization problem of Equation [20] can be expanded to solve for the scaled eye position $\tilde{o}$ across all frames in the contiguous sequence 220. Furthermore, by making some assumptions on the form of the reference frame mapping $M_R$ the reference image distortion can also be found. Making the assumption that the reference image distortion will be smooth and also only dependent upon the column number in the reference image the estimation problem for the continuous scaled eye position and the reference image distortion is given by the optimization problem of Equation [22], $$\min_{\tilde{o}, M_R} \sum_{n=0}^{N-1} \left\{ \int_0^{X_T} \sum_{k=0}^{K-1} g\left(\left\|P_R[\tilde{o}(x + nX_T) + q_k^{(n)}] + \right.\right.\right. \quad [22]$$

$$\tilde{o}(x + nX_T) + q_k^{(n)} - \frac{s_k}{2}\right\| \delta(x - x_k^{(n)}) +$$

$$\lambda \left\|\frac{d^2\tilde{o}(x + nX_T)}{dx^2}\right\|^2 dx \right\} + \int_0^X \gamma \left\|\frac{d^2 P_R(x)}{dx^2}\right\|^2 dx,$$

where $q_k^{(n)} = [x_k^{(n)}, y_k^{(n)}]^T$ are the points in the nth target frame where the shift measurements $s_k^{(n)}$ were measured, $p_k^{(n)}$ are the corresponding points in the reference frame where the shifts $s_k^{(n)}$ were measured, $\gamma$ is an smoothness regularization parameter for the reference image distortion, $\delta(x)$ is the Dirac delta function, and the reference offset function, $$P_R(p) = P_R(x) = M_R^{-1}(p) - p, \quad [23]$$

where $p = [x, y]^T$ and note that $P_R(x)$ is considered to be a function of x alone.

Equation [22] can now be solved for both the eye motion across the contiguous input sequence 220, $\tilde{o}(x)$, and the reference frame coordinate mapping, $M_R$, knowing the measurements from target frame to reference frame $s_k^{(n)}$ and appropriate values of the smoothness regularization parameters $\Delta$ and $\gamma$.

The above described processes are now explained in greater detail to allow an effective and efficient implementation. The application of some of these steps to an example sequence of images will also be discussed.

First Implementation

Figure 10:
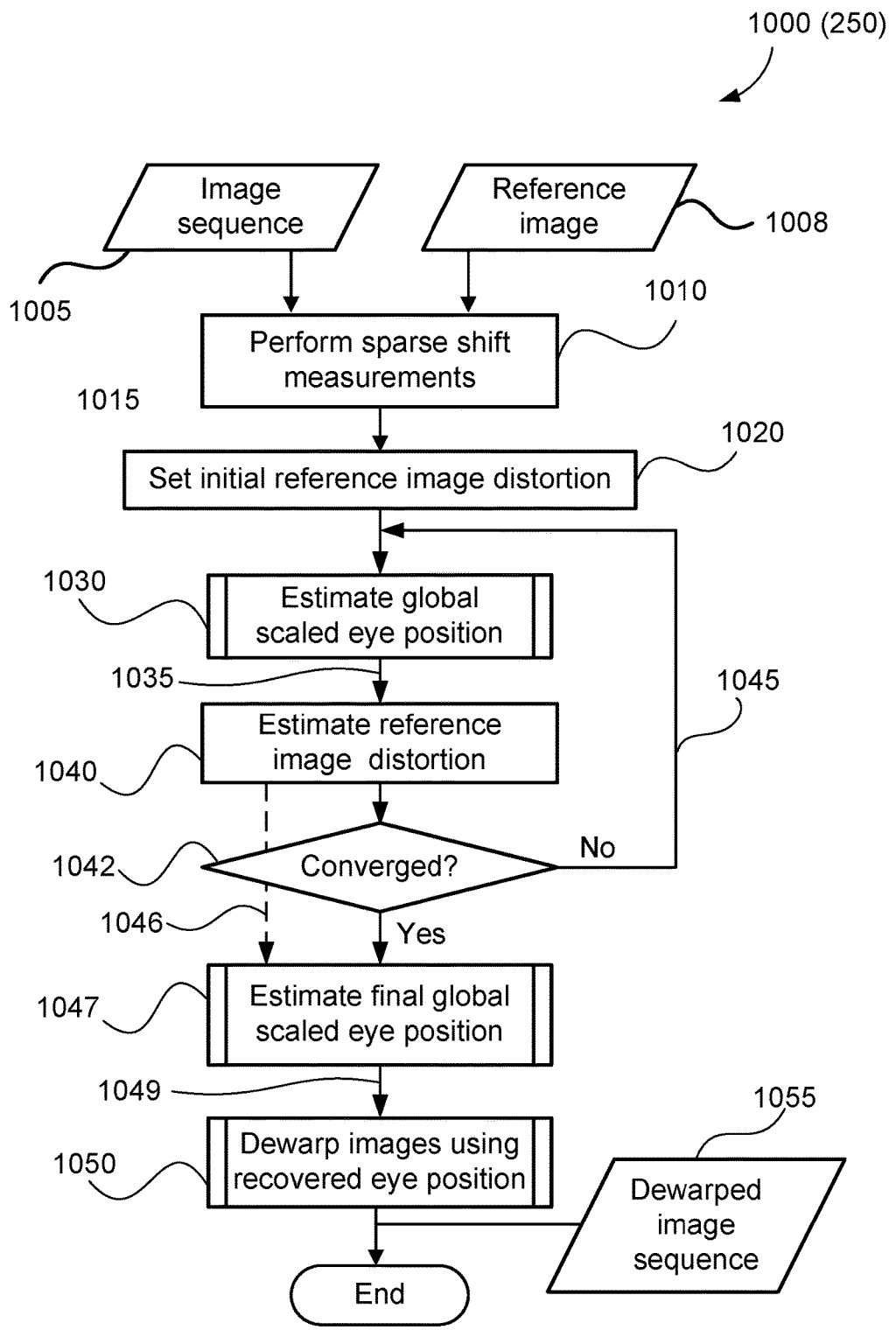
FIG. 10 is a flowchart showing a method for compensating a scene motion during the registration of a video sequence of AO-SLO images.

FIG. 10 shows a flowchart of a method 1000, used in step 250 to perform AO-SLO image registration with eye movement continuity. The method 1000 is preferably implemented as an application program stored in the HDD 1610 and executable by the processor 1605 and has two inputs, a contiguous sequence of target images 1005 and a reference image 1008, both of which may be stored in the HDD 1610 or memory 1606 after image capture and/or any preparatory or initial processing. In step 1010, the image sequence 1005 is processed one image at a time, in which measurements of shift at a plurality of locations, and preferably at least 3 locations throughout the selected image from image sequence 1005 are performed against the reference image 1008. An output of step 1010 is a set of initial relative shift measurements 1015 for each target image, and which represent high-resolution distortion within the relevant image frame of the sequence 1005.

It is now assumed that the distortion on the reference image is small and can be represented by an affine transform. Furthermore, this affine transform only varies with the x coordinate of the image therefore the reference image coordinate mapping can be written as Equation [24], $$M_R(q) = \begin{bmatrix} 1+a & 0 \\ b & 1 \end{bmatrix} q, \quad [24]$$

where a is the distortion parameter measuring horizontal stretching/compression and b is the distortion parameter measuring shear. The inverse mapping function from the retina coordinate space to the reference image coordinate space can then be written as Equation [25].

$$M_R^{-1}(r) = \begin{bmatrix} 1 - \dfrac{a}{1+a} & 0 \\ -\dfrac{b}{1+a} & 1 \end{bmatrix} r, \quad [25]$$

Now writing the coordinate vector in the nth target image as $q = [x, y]^T$, and setting the inverse warp parameters $\alpha = a/(1+a)$ and $\beta = b/(1+a)$, Equation [22] can be rewritten using Equations [25] and [23] as the optimization problem of Equation [26], $$\min_{\tilde{o}, \alpha, \beta} \sum_n \sum_k g\left(\{(1-\alpha)[\tilde{o}_x(x) + x_k^{(n)}] - x_k^{(n)} - s_{x,k}^{(n)}\}^2 + \right. \quad [26]$$

$$\{-\beta[\tilde{o}_x(x) + x_k^{(n)}] + [\tilde{o}_y(x) + y_k^{(n)}] - y_k^{(n)} - s_{y,k}^{(n)}\}^2\right) +$$

$$\int_0^{NX} \lambda_1 \left[\left(\frac{d^2\tilde{o}_x}{dx^2}\right)^2 + \left(\frac{d^2\tilde{o}_y}{dx^2}\right)^2\right] dx,$$

where $q_k^{(n)}=[x_k^{(n)},y_k^{(n)}]^T$ are the points in the nth target frame where the shift vectors $s_k^{(n)}$ were measured, $s_k^{(n)}=[s_{x,k}^{(n)}, s_{y,k}^{(n)}]^T$ is the measured shift vector, $\tilde{o}(x)=[\tilde{o}_x(x), \tilde{o}_y(x)]^T$ is the vector scaled eye position that is continuous across frames, and Δ is a smoothness regularization parameter for the eye movement, δ(x) is the Dirac delta function.

Now, using the least-squares error function $(l)=\frac{1}{2} l^2$, the variational optimization problem of Equation [26] is solved for the scaled eye position $\tilde{o}(x)$ and the reference frame affine distortion parameters α and β. Equation [26] may be solved by forming the Euler-Lagrange equations for the x and y components of the scaled eye position, $\tilde{o}_x(x)$ and $\tilde{o}_y(X)$ respectively, which can be written as Equations [27] and [28] and are coupled differential equations.

$$\sum_{n=0}^{N-1}\sum_{k=0}^{K-1} (\{(1-\alpha)^2[\tilde{o}_x(x)+x_k^{(n)}]-(1-\alpha)[x_k^{(n)}+s_{x,k}^{(n)}]\}+ \quad [27]$$

$$\beta\{\beta[\tilde{o}_x(x)+x_k^{(n)}]-[\tilde{o}_y(x)+y_k^{(n)}]+y_k^{(n)}+s_{y,k}^{(n)}\})$$

$$\delta[x-x_k^{(n)}-nX_T]+\mu\frac{d^4\tilde{o}_x}{dx^4}=0,$$

$$\sum_{n=0}^{N-1}\sum_{k=0}^{K-1}\{\beta[\tilde{o}_x(x)+x_k^{(n)}]-[\tilde{o}_y(x)+y_k^{(n)}]+y_k^{(n)}+s_{y,k}^{(n)}\}\delta[x-x_k^{(n)}-nX_T]+ \quad [28]$$

$$\mu\frac{d^4\tilde{o}_y}{dx^4}=0.$$

Furthermore, the reference image affine distortion parameters α and β are given by Equations [29] and [30].

$$\alpha=\frac{\sum_n\sum_k [o_x(x_k^{(n)}+nX_T)+x_k^{(n)}][o_x(x_k^{(n)}+nX_T)-s_{x,k}^{(n)}]}{\sum_n\sum_k [o_x(x_k^{(n)}+nX_T)+x_k^{(n)}]^2}, \quad [29]$$

$$\beta=\frac{\sum_n\sum_k [o_x(x_k^{(n)}+nX_T)+x_k^{(n)}][o_y(x_k^{(n)}+nX_T)-s_{y,k}^{(n)}]}{\sum_n\sum_k [o_x(x_k^{(n)}+nX_T)+x_k^{(n)}]^2}. \quad [30]$$

Equation [26] can then be solved by direct solution of the nonlinear Euler-Lagrange equations—Equations [27], [28], [29], and [30]—for all unknowns, namely the x and y components of the scaled eye position, $\tilde{o}_x(x)$ and $\tilde{o}_y(X)$, and the reference frame affine distortion parameters α and β. This process can be computationally expensive. However, if the reference frame distortion is considered to be constant, then Eqn. [26] can be solved computationally efficiently using a vector smoothing spline interpolation algorithm. This gives an efficient algorithm to solve Eqn. [26] by iteratively solving for the solution of the x and y components of the scaled eye position, $\tilde{o}_x(x)$ and $\tilde{o}_y(x)$, with the reference frame affine distortion parameters α and β fixed, then solving for the reference frame affine distortion parameters α and β with the x and y components of the scaled eye position, $\tilde{o}_x(x)$ and $\tilde{o}_y(x)$, fixed.

This iterative process is now described with reference to FIG. 10. In step 1020, the reference frame distortion (warp) is initialized to the identity transform. After step 1020, a loop structure is preferably employed by method 1000 to solve iteratively for the global scaled eye position. The loop implements an iterative process forming an optimization procedure which involves solving two equations in step 1030 and 1040, where the scaled eye position function is related to the distortion on the nth image by Equation [21]. Step 1030 determines an initial eye movement trajectory to form an estimate of the global scaled eye position 1035 for the sequence of image frames from the corresponding sparse shift measurements 1015 calculated at step 1010. Step 1030, on an initial or first execution, forms the estimates 1035 in combination with the initial reference image distortion as set at step 1020. Thereafter, where the loop is implemented, step 1030 uses a current estimate of the reference image distortion 1045 formed using the assumption of smoothness of eye position between the frames in the input image sequence. Step 1040 then calculates a new estimate for the reference image distortion 1045 using the previously calculated global scaled eye position 1035. Steps 1030 and 1040 are performed at least once for each image frame in the sequence 1005. Where the loop structure is not implemented, as indicated by the dashed line 1046, the method 1000 proceeds from step 1040 to step 1047.

Desirably however, steps 1030 and 1040 are iteratively performed using the updated reference image distortion 1045 which is applied to each frame of the sequence 1005 until at least one convergence criteria is met. Step 1042 tests for convergence of the updated reference frame distortion 1045. One test is a percentage change of the distortion 1045 such that where the percentage change for an iteration falls below a predetermined level (e.g. less than 10%), then the distortion is deemed to have converged. Another criteria can be the number of iterations reaching a predetermined maximum number (e.g. 5). Desirably, all convergence criteria are tested simultaneously on each iteration. Steps 1040 and 1040 operate to select a reference frame distortion which provides a smooth transition for the initial eye movement trajectory Once the iterative process in steps 1030 and 1040 converges at step 1042, the method 1000 proceeds to step 1047 where an estimate of the final global scaled eye position 1049 is determined from the most recent position 1035 and the converged distortion value 1045. Step 1050 then follows where the target images are de-warped according to the estimated global scaled (recovered) eye position $\tilde{o}(x)$, being the iteratively converged current value of the global estimate of eye position 1049. This estimated position is a curve, such as the curve O(t) as seen in FIG. 6. Method 1000 then ends after step 1050, outputting a de-warped image sequence 1055. The global eye position recovery step 1030 will be described further in detail with reference to FIG. 11. The image de-warping step 1050 will be described further in detail with reference to FIG. 12.

Method 1100, used in step 1030 to estimate global offset mapping across all input frames 120 will now be described with reference to FIG. 11. The method 1100 takes two inputs, a set of shift measurements 1110 (1015) obtained in step 1010 and the current estimate of the reference image distortion 1120 (1045). In the first iteration, the reference frame distortion can be initialized to be undistorted, namely α=β=0, or any approximate information about the reference frame distortion can be used. In step 1130, the relative shift measurements 1110 and reference image distortion 1120 values are used to produce interpolation (shift) data 1135 for the eye position, o(x). An outlier removal process is then desirably applied to absolute shift values in step 1140. The absolute shift values are calculated using the relative shift values s from Equations [26] and [27] and the reference frame distortion parameters alpha (α) and beta (β) from Equations [28] and [29]. In the case of using the squared error function, $g(l)=\frac{1}{2} l^2$, in Equation [26] the outlier removal process 1140 is preferably implemented using the RANSAC algorithm; however, any other suitable algorithm may be applied. In the case of using a M-estimator error function in Equation [26] the remove outliers step 1140 can be combined with the interpolation step 1150 to form an iteratively reweighted least-squares solution of Equation [26]. Method 1100 then moves to step 1150, in which the shift inliers are interpolated using a vector smoothing spline algorithm to efficiently solve Equation [26]. Method 1100 ends after step 1150 with the formation of a current estimate of global eye position 1035.

In step 1050, the estimated (interpolated) scaled eye position 1049 and estimated reference warp ($\alpha$, $\beta$) are now known and the input frames can now be remapped to the approximate retinal coordinate system of FIG. 9. To remap the input images to the retinal coordinate system it is noted that the absolute coordinate mappings for reference and target frames give the location in the retinal coordinate system of a pixel in the image coordinate system. Therefore, the remapping process of step 1050 can be thought of as taking pixels in the target frames at the target frame coordinates and "moving" them to the coordinate given by the absolute mapping to the retinal coordinate system.

Representing the intensity of the nth input image as the continuous function, $I_n(q)$, where q is the vector coordinate in the input image coordinate system, then the output image for each frame $O_n(r)$, where r is the vector coordinate in the input image coordinate system, is given by Equation [31], $$O_n[M_n(q)] = I_n(q), \quad [31]$$

where $M_n(q)$ is the estimated absolute coordinate mapping given by Equation [21].

However, in the case of input images that are composed of a discrete set of pixels then Equation [31] cannot be used directly to form the remapped image $O_n$, otherwise there will be severe aliasing artefacts. There are two standard methods to remap a discrete image using a coordinate mapping function: the first is to iterate through all pixels $r=(\tilde{x},\tilde{y})$ in the remapped image $O_n$ and calculate the inverse coordinate mapping $M_n^{-1}(r)$ to determine the coordinate in the input image coordinate system that this pixel should be sampled from. Typically $M_n^{-1}(r)$ will be a non-integer coordinate and the input image $I_n$ can be interpolated to find the approximate value.

The second method is to use the forward mapping $M_n(q)$ directly by iterating through all pixels $q=(x,y)$ in the input image $I_n$ and calculating the coordinate mapping $M_n(q)$ to determine the coordinate in the destination image coordinate system and adding a kernel function multiplied by the intensity of the input image at the current coordinate $I_n(q)$ to the destination image $O_n$ offset by the typically non-integer destination coordinate $M_n(q)$. This kernel function can be any of a number of known functions with compact support; for example, often a Gaussian function is used as is given by Equation [32], $$K(u) = \exp\left[-\frac{\|u\|^2}{2d^2}\right], \quad [32]$$

where d is the width of the Gaussian function.

The output image can then be formed from a summation of the contributions of a convolution of the input pixels with a sub-pixel shifted kernel function K(u). This can be written as an equation for the output pixel $r=(\tilde{x},\tilde{y})$ as given by Equation [33], $$O_n(r) = \frac{\sum_{p \in \mathcal{N}(r)} K(M_n(p)-r)I(p)}{\sum_{p \in \mathcal{N}(r)} K(M_n(p)-r)}, \quad [33]$$

where $\mathcal{N}(r)$ is a set of pixels in the neighbourhood of r where the kernel function has significant support. The denominator of Equation [33] is a normalization function formed by the summation of the kernel function with at the same mapping points as the numerator. This function is used to compensate for the differences in the density of the coordinate mapping. As a consequence the normalization function can be expressed as an image, a normalization image.

Figure 12:
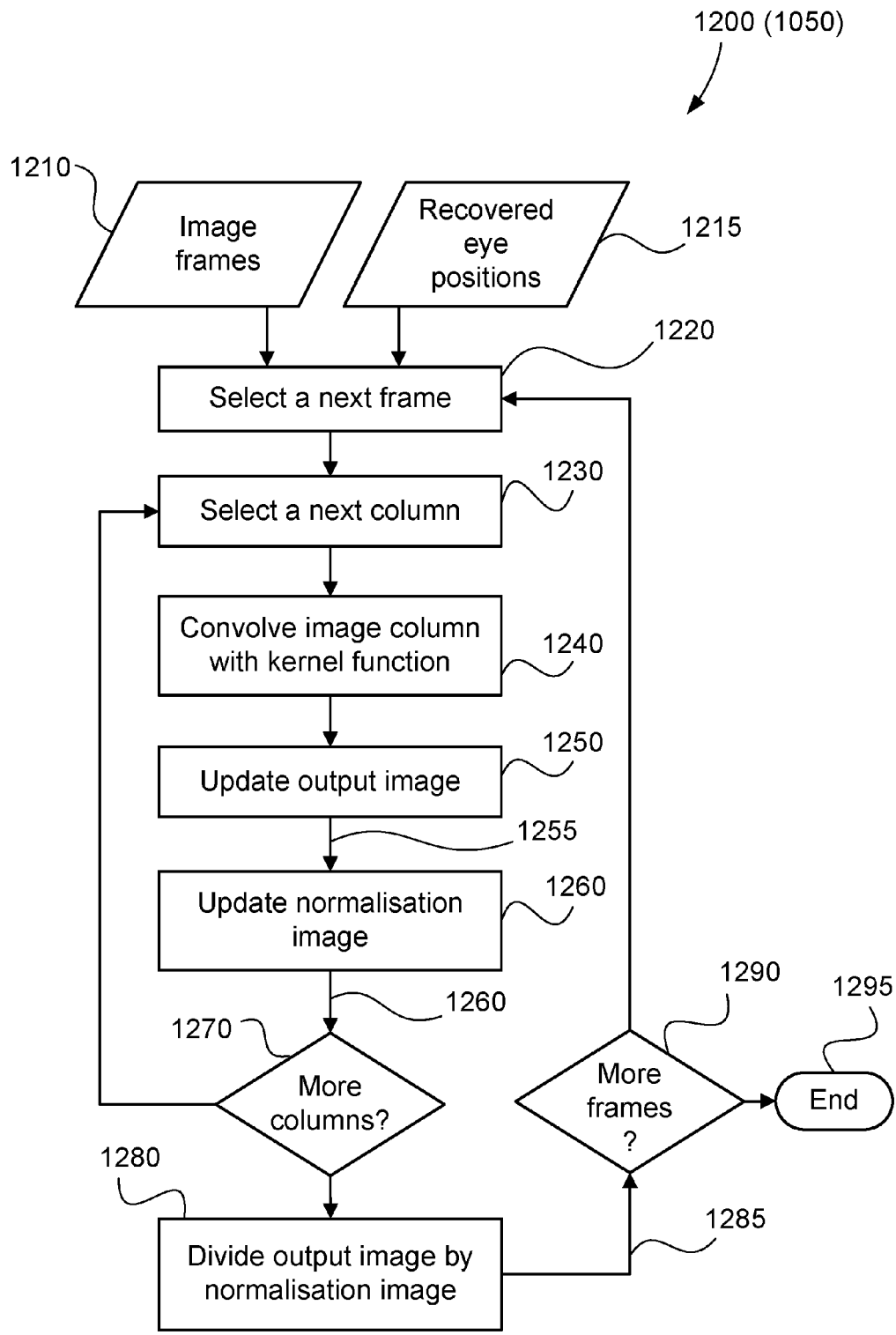
FIG. 12 is a flowchart showing a method for de-warping images based on recovered eye position.

This method of image remapping, also called image gridding, is used in step 1050 and is described further with reference to FIG. 12. The method 1200 takes two inputs, a set of target image frames 1210, being based upon the input image sequence frames 220, and the recovered global eye position curve 1215 (1049). The method 1200 employs a double loop structure which iterates over all the target frames 1210, and for each target frame the method 1200 iterates over all the columns within the selected target frame. The iteration over the target frames begins in step 1220, in which a next target frame is selected. The method 1200 then proceeds to step 1230 in which a next column within the currently selected target frame is selected. The fact that the scaled eye position is constant over the column of the target image is now used to accelerate the remapping. In step 1240, the selected column is convolved with a 2D kernel image that can be calculated as the kernel function offset by a column-dependent sub-pixel offset as given by Equation [34]:

$$K_c(i,j) = K(x_{sp}+i, y_{sp}+j), \quad [34]$$

where sub-pixel offsets for the column x of the nth target frame is given by $x_{sp}=M_x^{(n)}(x)-\lfloor M_x^{(n)}(x) \rfloor$, and $y_{sp}=M_y^{(n)}(x)-\lfloor M_y^{(n)}(x) \rfloor$. The convolved column is then added to the output image and offset by an amount equal to $\lfloor M_x^{(n)}(x) \rfloor$-x in the x direction and $\lfloor M_y^{(n)}(x) \rfloor$-y in the y direction in step 1250 to produce an updated output image 1255. The method 1200 proceeds to update a normalization image in step 1260 by adding the kernel image of Equation [34] convolved with a column of all ones. This forms an updated normalization image 1260 for the current target image. In step 1270, the method 1200 checks if there are further columns in the target image to be processed. If there is, the processing of method 1200 returns to step 1230, otherwise method 1200 continues to step 1280. In step 1280, the updated output image 1255 is divided by the updated normalization image 1260 to form the final remapped image 1285. In step 1290, the method 1200 checks if there are further target images to be processed. If there is, the processing of method 1200 returns to step 1220, otherwise method 1200 ends in step 1295.

The net result of the method 1200 is that each frame of the input image sequence 220 (1210) is modified according to the eye position curve 1049 (1215) to form an output frame 1285 that is corrected for eye movement that occurred during image capture.

Second Implementation

An alternate implementation for step 250 to perform AO-SLO image registration with eye movement continuity will now be described in detail below with reference to a method 1300 schematically shown in FIG. 13. The method 1300 has two inputs, a contiguous sequence of target images 1305 (220) and a reference image 1308 (240). In step 1310, the target images 1305 are processed one image at a time, in which measurements at locations throughout a current selected image from the target images 1305 are performed against the reference image 1308. The output of step 1310 is a set of relative shift measurements 1315 for each target image.

Figure 14:
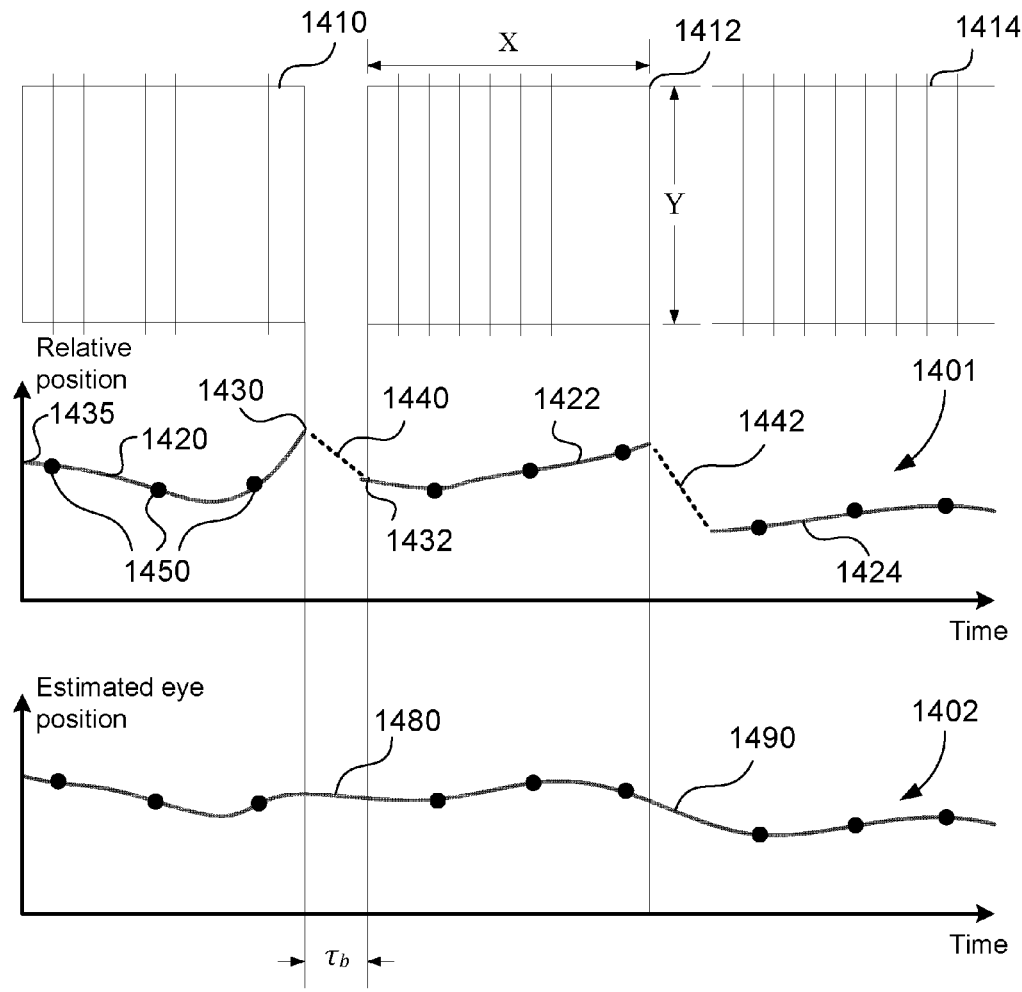
FIG. 14 is an illustration of the relative position between target and reference images and the interpolation of the estimated eye position using an estimated reference image distortion.

Next the method 1300 moves to step 1320 where a coordinate mapping 1325 relative to the reference image 1308 for each image in the target images 1305 is calculated individually using extrapolation to estimate the relative positions in non-overlapping region of each target image. The coordinate mapping 1325 is therefore an estimated mapping. The functionality of step 1320 is illustrated in FIG. 14 where the estimated relative position of each column in three target images 1410, 1412, and 1414 are calculated. For example, the target image 1410 has relative position measurements 1450 made between locations in target image regions locations in the reference image. These relative position measurements are used to interpolate a relative position curve 1420 within each target image and also extrapolate the curve 1420 to the edges of the target image 1410, such as the concluding edge 1430. A similar extrapolation is performed to a starting edge 1435 of the target image 1410. Further interpolation between frames is performed using extrapolated curves to form an initial complete eye position curve 1401, i.e. inter-frame interpolation curves 1440 and 1442 are calculated by interpolating the intra-frame extrapolated curves 1420, 1422 and 1424.

The method 1300 now moves to step 1330 where the reference distortion 1335 is calculated. In this step, a reference frame distortion 1335 is sought that minimizes the sum of the gradient squared of the inter-frame interpolated position between all frames, e.g. the curves 1440 and 1442 in FIG. 14. It can be seen that without considering the reference frame distortion, namely taking the reference frame distortion to be the identity, the linear interpolated position between the frames can be made by connecting the extrapolated position 1430 at the end of the first target image 1410 to the extrapolated position 1432 at the start of the second target image 1412. The gradient of this inter-frame interpolated position 1440 is, in general, larger than if the reference image distortion were known and used to aid the interpolation. A reference frame distortion can then be calculated by minimizing the inter-frame gradients that have been calculated from the initial complete eye position curve, $\tilde{o}(x)$. However, this process can be done iteratively, after the first iteration a further interpolated complete eye position curve can be used to calculate a further reference frame distortion in accordance with Equations [37] and [38]. The further interpolated complete eye position is calculated using a previously determined reference frame distortion using Equation [13].

The sum of the gradient squared of the estimated eye position between frames is given by Equation [35] below.

$$\sum_{n=0}^{N-2} \frac{\|\tilde{o}((n+1)X_T) - \tilde{o}(X + nX_T)\|^2}{\tau_b^2}.$$  [35]

where $\tilde{o}(x)=[\tilde{o}_x(x), \tilde{o}_y(x)]^T$ is the vector scaled eye position, $\tilde{o}(nX_T+X)$ is the extrapolated eye position at the end of the nth frame, $\tilde{o}((n+1)X_T)$ is the extrapolated eye position at the start of the n+1th frame, n is the frame number, $X_T$ is the pixel-scaled frame time as given by Equation [4], N is the total number of frames, and $\tau_b$ is the blanking time between frames.

Taking into account a reference frame distortion, $M_R$, the estimated eye position can be written in terms of the relative positions between each target frame and the reference frame using Equation [19]. Then the reference frame distortion $M_R$, can be estimated by minimizing the expression for the total summed gradient squared between all frames, as given by Equation [36] below. Initial gradients between the frames can be obtained from the initial complete eye position curve 1401 generated by inter-frame interpolation of the intra-frame extrapolated curves 1420, 1422 and 1424.

$$\min_{M_R} \sum_{n=0}^{N-2} \frac{\|M_R \cdot M_{n+1}(0) - M_R \cdot M_n(q_X) + q_X\|^2}{\tau_b^2}.$$  [36]

where $q_x=[X, 0]^T$ is a vector representing the location of the last column in the target image, $M_n(q_x)$ is the absolute mapping function evaluated at the end of the nth frame as obtained by intra-frame extrapolation, and $M_{n+1}(0)$ is the absolute mapping function evaluated at the start of the n+1$^{th}$ frame as obtained by intra-frame extrapolation.

It is now assumed that the distortion on the reference image is small and can be represented by an affine transform. Furthermore, this affine transform only varies with the x coordinate of the image therefore the reference image coordinate mapping can be written as Equation [24].

Solving the minimization problem of Equation [36] for the affine reference frame distortion of Equation [24] and writing the vector relative mapping between target image n and the reference image as $m_n(x)=[m_n^{(x)}(x), m_n^{(y)}(x)]^T$ leads to two equations for the affine parameters a and b, representative of the reference image distortion 1335, given by Equations [37] and [38] below, $$a = \frac{\sum_{n=0}^{N-2} [m_{n+1}^{(x)}(0) - m_n^{(x)}(X) + X][m_{n+1}^{(x)}(0) - m_n^{(x)}(X)]}{\sum_{n=0}^{N-2} [m_{n+1}^{(x)}(0) - m_n^{(x)}(X)]^2}.$$  [37]

$$b = \frac{\sum_{n=0}^{N-2} [m_{n+1}^{(y)}(0) - m_n^{(y)}(X)][m_{n+1}^{(x)}(0) - m_n^{(x)}(X)]}{\sum_{n=0}^{N-2} [m_{n+1}^{(x)}(0) - m_n^{(x)}(X)]^2}$$  [38]

where X is the x-location of the last column in the target image, $m_n^{(x)}(X)$ and $m_n^{(y)}(X)$ are the relative mapping functions for the x and y coordinates respectively evaluated at the end of the nth frame as obtained by intra-frame extrapolation, and $m_{n+1}^{(x)}(0)$ and $m_n^{(y)}(0)$ are the relative mapping functions for the x and y coordinates respectively evaluated at the start of the n+1th frame as obtained by intra-frame extrapolation.

Figure 11:
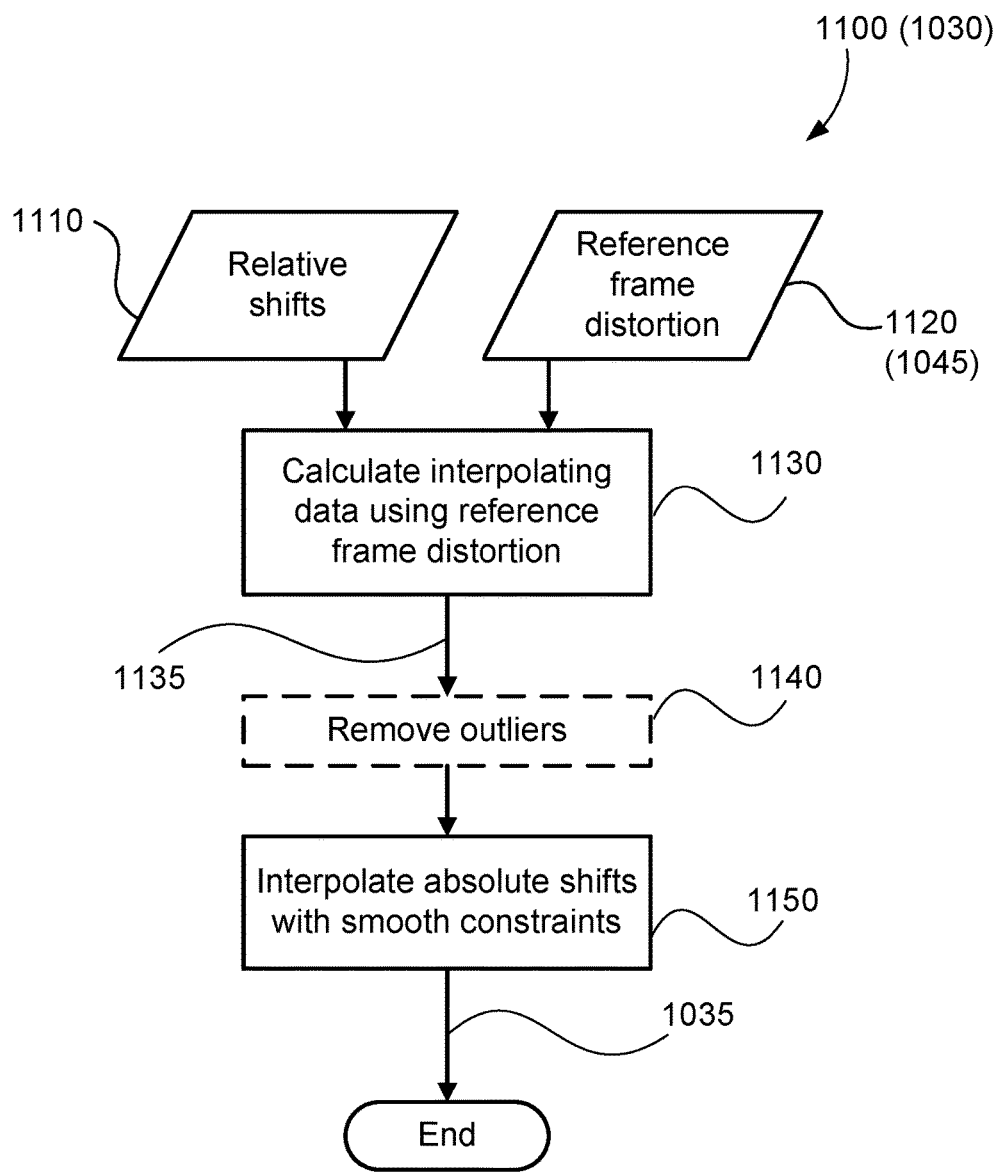
FIG. 11 is a flowchart showing a method for recovering global eye position over time.

Method 1300 now proceeds to step 1340 where the reference image distortion parameters 1335, given by a and b calculated in Equations [37] and [38] above are used to estimate the global scaled eye position $\tilde{o}(x)$ 1345 across all frames, as for example implemented by method 1100 shown in FIG. 11 and described previously. This is a global eye movement trajectory for the sequence of images. The result step 1340 for the example of FIG. 14 is the estimated eye position shown in graph 1402 of FIG. 14 that is smooth across frame boundaries and which has minimized gradient in the inter-frame times 1480 and 1490. The overall effect, as clearly seen in FIG. 14, is that the disclosed arrangements, and particularly the estimation of frame distortion provide for smooth transitions between image frames in the presence of eye movement.

Finally, method 1300 moves to step 1350 where the target images 1305 are dewarped using the estimated scaled eye position as implemented by method 1200 shown in FIG. 12 and described previously. This provides a de-warped image sequence 1355 where the AO-SLO images are compensated for distortions caused by eye movement that occurred during image capture.

Advantage

Figure 15:
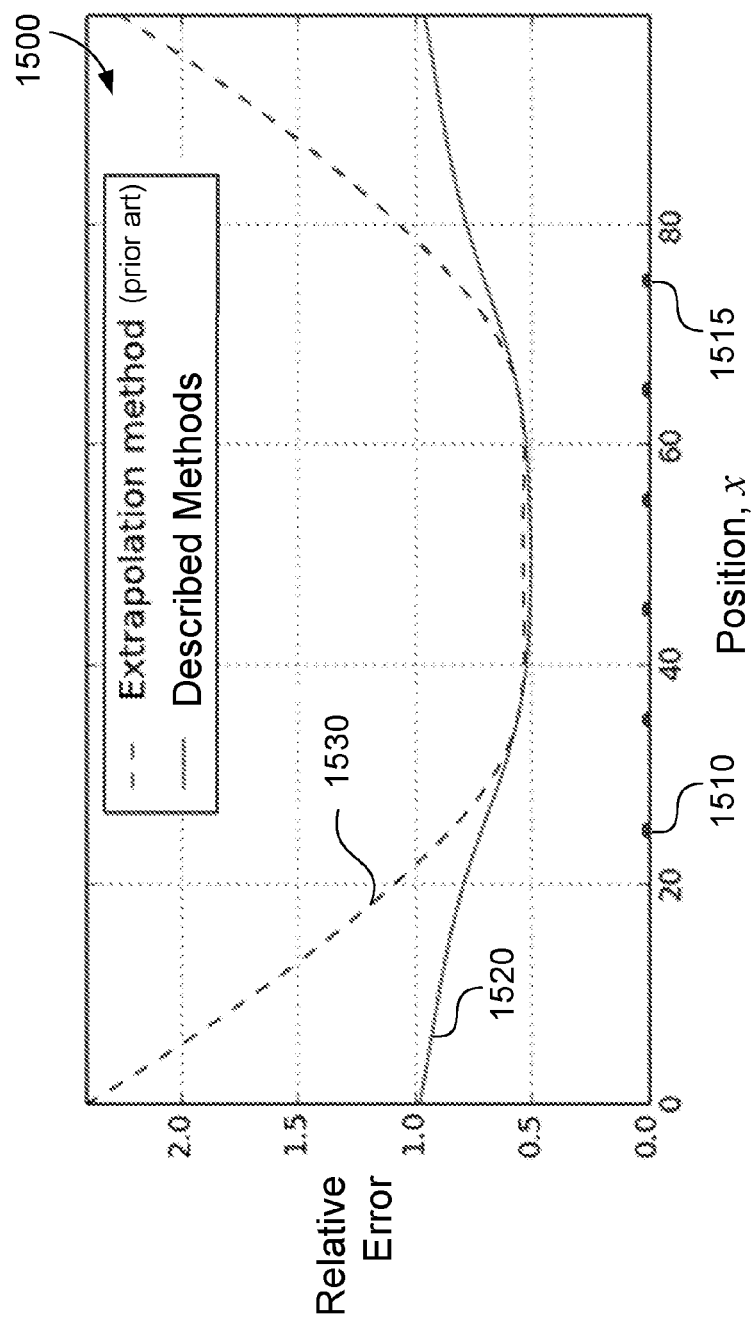
FIG. 15 is a graph showing the relative errors of the eye motion estimation across many frames using the invention and a prior-art method.

The performance of the above described arrangements is shown in a graph 1500 of FIG. 15. The graph 1500 shows the relative errors of the estimated eye position curves using traditional (prior art) extrapolation approaches 1530 and the presently described method of eye movement continuity approaches 1520. In this comparative example, the present inventor compared the performance of registration between a 400×400 pixel reference frame and 16 of 400×400 pixel target frames that were distorted by a continuous simulated eye motion. Four shift measurements were taken each of the x positions indicated by semi-circles 1510 and the accuracy of alignment was calculated across the entire target frame. For the extrapolation method the coordinate mapping function values beyond the last measurement locations in each frame 1510 and 1515 were calculated by extrapolation from the measurement values taken inside each frame individually. For the frame continuity method the coordinate mapping function values beyond the last measurement locations in each frame 1510 and 1515 were calculated by interpolation across the entire frame sequence using the process detailed in the first implementation.

The graph 1500 shows that for simulated tests averaging the relative error in the calculated coordinate mapping function over 1000 random realizations of eye motion that the presently disclosed arrangements can reduce the extrapolation error in non-overlapping regions by around 50%.

Figure 13:
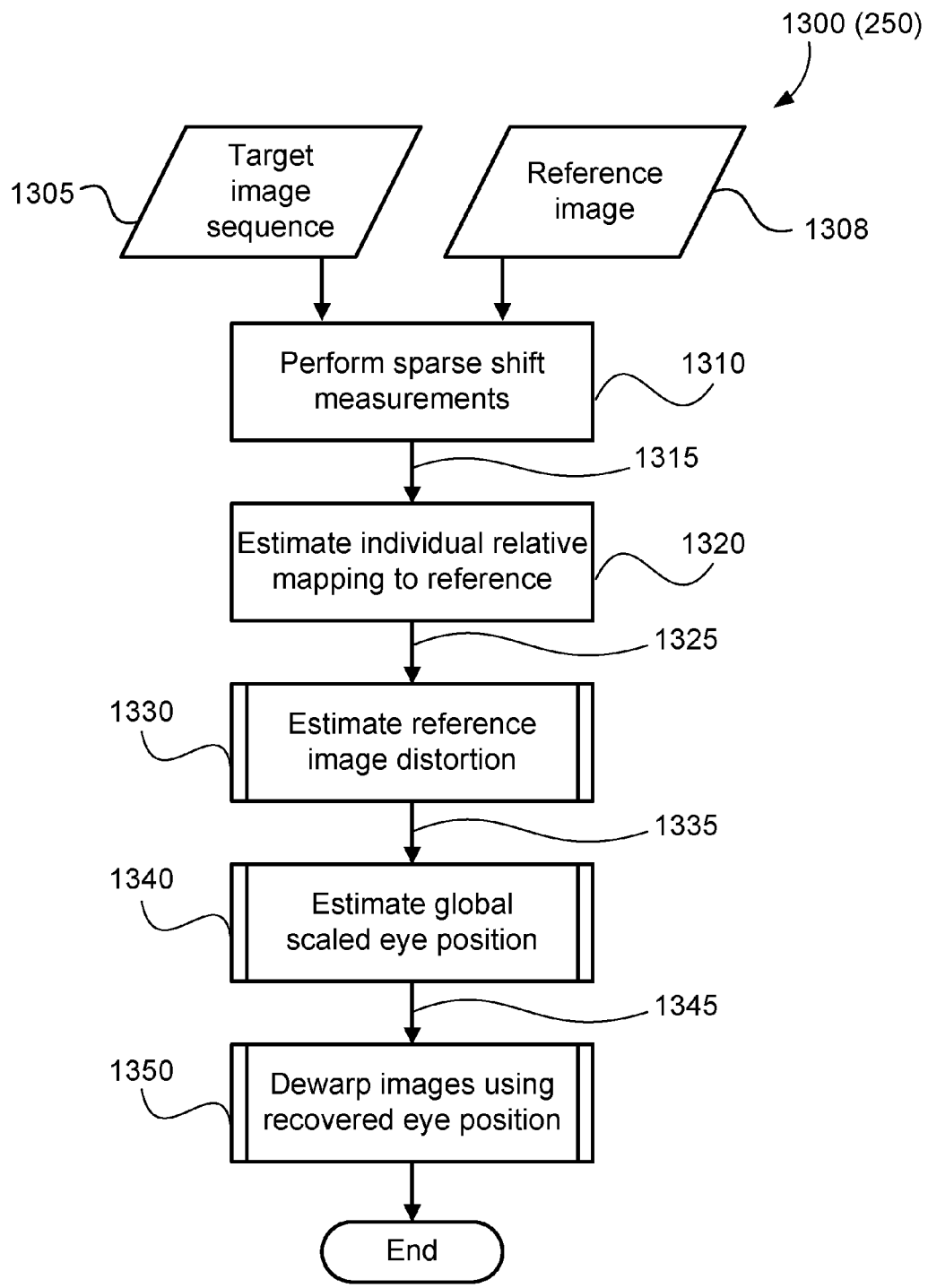
FIG. 13 is a flowchart showing an alternative method for compensating a scene motion during the registration of a video sequence of AO-SLO images.

The implementations of FIGS. 10 and 13 each draw upon a mutual dependency between the reference frame distortion and the determined eye movement trajectory using the predetermined dynamics of the eye and the shifts within and/or between the frames of sequence of images, as given explicitly by Equations [13], [22], [26], [35] and [36]. In the implementation of FIG. 10, the mutual dependency is concentrated upon the iterative processing using the distortion 1045 as a feedback element. In the implementation of FIG. 13, the mutual dependency arises is drawn upon by the smoothing if the transitions between adjacent image frames.

In specific implementations, the dewarped sequence of images, once determined by the processor 1605 can be stored in the HDD 1610 for reproduction. Such reproduction may be directly via the video display 1614 to thereby reproduce a substantially smooth sequence of retinal images. In other implementations, the actual eye movement trajectory, O(t), for example seen in FIG. 6 may be similarly stored on the HDD 1610 and displayed on the display device 1614 to assist in ophthalmic diagnosis of the patient.

In certain implementations, the arrangements described may further comprise using the determined eye movement trajectory to identify a further reference frame. This can include estimating the scaled eye position across all input frames using a possibly reduced number of measurements and determining the frame with least distortion, corresponding to a frame with low total gradient in the eye-position curve, and using this frame as a reference frame in a further eye-motion estimation process.

INDUSTRIAL APPLICABILITY

The arrangements described are applicable to the computer and data processing industries and particularly for the registration of images across frame boundaries. The disclosed methods for compensating for distortion, in a plurality of retinal image frames, as a result of eye movement provides for the use of the determined eye movement trajectory to adjust portions of the frames outside the areas of overlap. The arrangements disclosed have particular application to AO-SLO image capture. This notwithstanding, the approaches disclosed herein can be used for image registration in a wide variety of applications and especially video images captured using a rolling shutter camera where image stabilization is desired. This can included mobile telephone cameras and the like.

The foregoing describes only some embodiments of the present invention, and modifications and/or changes can be made thereto without departing from the scope and spirit of the invention, the embodiments being illustrative and not restrictive.

I claim:

1. A computer-implemented method of compensating for image distortion, in a plurality of retinal image frames, as a result of eye movement, the method comprising:
   (a) receiving at least one reference image frame and the plurality of image frames capturing substantially the same portion of the eye;
   (b) for each image frame of the plurality of image frames, determining, using a processor, a plurality of shifts relative to the reference image frame, the shifts representing image distortion within each image frame of the plurality of image frames with respect to the reference image frame;
   (c) determining, using the processor, an initial eye movement trajectory based on the shifts within each image frame of the plurality of image frames;
   (d) estimating, using the processor, image distortion within the reference image frame using the initial eye movement trajectory and the plurality of shifts within each image frame of the plurality of image frames;
   (e) estimating, using the processor, a current eye movement trajectory based on the estimated image distortion within the reference image frame, and the shifts within each image frame of the plurality of image frames to provide a smooth transition between the plurality of image frames in the eye movement, wherein a magnitude of a gradient of the current eye movement trajectory during an inter-frame period is reduced; and
   (f) compensating, using the processor, for image distortion within each image frame of the plurality of image frames using the current eye movement trajectory.

2. A method accord to claim 1, further comprising repeating steps (d) and (e) at least once to determine an iterated current eye movement trajectory.

3. A method according to claim 1, wherein the estimating of steps (c) and (e) is further based on predetermined dynamics of the eye.

4. A method according to claim 3, wherein the predetermined dynamics of the eye include at least one of velocity, acceleration and speed.

5. A method according to claim 1, further comprising using a smoothing spline interpolation between the plurality of shifts within each of the plurality of image frames to determine a current eye movement trajectory.

6. A method according to claim 1, further comprising using the determined eye movement trajectory to identify a further reference image frame.

7. A method according to claim 1, further comprising displaying at least one of the determined eye movement trajectory and the compensated sequence of eye images.

8. A method according to claim 1, wherein the plurality of image frames are captured successively and the reference image frame is selected from at least one of any of the captured image frames.

9. A method according to claim 8, wherein the reference image frame is generated by averaging multiple frames.

10. A computer-implemented method of compensating for image distortion, in a plurality of image frames, as a result of eye movement, the method comprising:
   receiving at least one reference image frame and the plurality of image frames capturing substantially the same portion of the eye;
   for each image frame of the plurality of image frames, determining, using a processor, a plurality of shift values relative to the reference image frame, the shift values representing image distortion within each image frame of the plurality of image frames with respect to the reference image frame;
   determining, using the processor, an individual eye movement trajectory for each image frame of the plurality of image frames and a transition between pairs of adjacent ones of the plurality of image frames, the eye movement trajectory being based at least on the image distortion within each image frame of the plurality of image frames;
   determining, using the processor, image distortion of the reference image frame from the transitions; and
   compensating, using the processor, for image distortion in said plurality of image frames using the determined eye movement trajectories and the image distortion of the reference image frame, wherein a magnitude of a gradient of the determined eye movement trajectories during an inter-frame period is reduced based on the determined image distortion of the reference image frame.

11. A method according to claim 10, wherein the compensating comprises:
   estimating a global eye movement trajectory using the determined image distortion of the reference image frame; and
   dewarping the plurality of images using the global eye movement trajectory.

12. A method according to claim 10, wherein the estimating of the eye movement trajectory is further based on predetermined dynamics of the eye.

13. A method according to claim 10, wherein the individual eye movement trajectory for a frame is determined by extrapolating relative shifts of two adjacent consecutive frames from the plurality of image frames.

14. A computer-implemented method of compensating for image distortion, in a plurality of image frames, as a result of eye movement, the method comprising:
   receiving at least one reference image frame and the plurality of image frames capturing substantially the same portion of the eye, the plurality of image frames being captured sequentially and substantially continuously;
   for each image frame of the plurality of image frames, determining, using a processor, a plurality of shifts within each image frame of the plurality of image frames with respect to the reference image frame;
   establishing, using the processor, a mutual dependency between image distortion of the reference image frame and an eye movement trajectory using predetermined dynamics of the eye and a plurality of shifts within each image frame of the plurality of image frames;
   determining, using the processor, an eye movement trajectory in accordance with the established mutual dependency using the image distortion of the reference image frame, which allows for a smooth transition, in the determined eye movement trajectory, between pairs of adjacent other image frames and allows for a magnitude of a gradient of the eye movement trajectory during an inter-frame period to be reduced; and
   compensating, using the processor, for image distortion in said plurality of image frames using the determined eye movement trajectory.

15. A method according to claim 14, wherein the plurality of shifts are determined in an area of overlap between said frame and the reference image frame.

16. A method according to claim 15, wherein the compensating comprises using the determined eye movement trajectory to adjust portions of the frames outside the areas of overlap.

17. A non-transitory computer readable storage medium having a program recorded thereon, the program being executable by a processor to compensate for image distortion in a plurality of retinal image frames, as a result of eye movement, the program comprising:
   code for receiving at least one reference image frame and the plurality of image frames capturing substantially the same portion of the eye;
   code, executable for each image frame of the plurality of image frames, for determining a plurality of shifts relative to the reference image frame, the shifts representing image distortion within each image frame of the plurality of image frames with respect to the reference image frame;
   code for determining an initial eye movement trajectory based on the shifts within each image frame of the plurality of image frames;
   code for estimating image distortion within the reference image frame using the initial eye movement trajectory and the plurality of shifts within each image frame of the plurality of image frames;
   code for estimating a current eye movement trajectory based on the estimated image distortion within the reference image frame, and the shifts within each image frame of the plurality of image frames to provide a smooth transition between the plurality of image frames in the eye movement, wherein a magnitude of a gradient of the current eye movement trajectory during an inter-frame period is reduced;
and
   code for compensating for image distortion within each image frame of the plurality of image frames using the current eye movement trajectory.

18. An apparatus for compensating for image distortion, in a plurality of retinal image frames, as a result of eye movement, the apparatus comprising:
   a processor; and
   a memory having a program recorded thereon and being executable by the processor to perform the compensating for image distortion, the program comprising:

code for receiving at least one reference image frame and the plurality of image frames capturing substantially the same portion of the eye;

code, executable for each image frame of the plurality of image frames, for determining a plurality of shifts relative to the reference image frame, the shifts representing image distortion within each image frame of the plurality of image frames with respect to the reference image frame;

code for determining an initial eye movement trajectory based on the shifts within each image frame of the plurality of image frames;

code for estimating image distortion within the reference image frame using the initial eye movement trajectory and the plurality of shifts within each image frame of the plurality of image frames;

code for estimating a current eye movement trajectory based on the estimated image distortion within the reference image frame, and the shifts within each image frame of the plurality of image frames to provide a smooth transition between the plurality of image frames in the eye movement, wherein a magnitude of a gradient of the current eye movement trajectory during an inter-frame period is reduced; and code for compensating for image distortion within each image frame of the plurality of image frames using the current eye movement trajectory.

19. An adaptive optics scanning-laser ophthalmoscope (AO-SLO) comprising the apparatus according to claim 18.

* * * * *